(12) United States Patent
Schachtel

(10) Patent No.: US 9,044,465 B2
(45) Date of Patent: *Jun. 2, 2015

(54) USE OF ANALGESIC POTENTIATING COMPOUNDS TO POTENTIATE THE ANALGESIC PROPERTIES OF AN ANALGESIC COMPOUND

(71) Applicant: SCHABAR RESEARCH ASSOCIATES LLC, Jupiter, FL (US)

(72) Inventor: Bernard P. Schachtel, Jupiter, FL (US)

(73) Assignee: SCHABAR RESEARCH ASSOCIATES, LLC, Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/291,037

(22) Filed: May 30, 2014

(65) Prior Publication Data

US 2014/0275188 A1  Sep. 18, 2014

Related U.S. Application Data

(63) Continuation of application No. 12/811,528, filed as application No. PCT/US2009/030079 on Jan. 5, 2009, now Pat. No. 8,771,643.

(60) Provisional application No. 61/019,025, filed on Jan. 4, 2008.

(51) Int. Cl.
| | |
|---|---|
| A61K 31/426 | (2006.01) |
| A61K 45/06 | (2006.01) |
| A61K 31/167 | (2006.01) |
| A61K 31/415 | (2006.01) |
| A61K 31/485 | (2006.01) |
| A61K 31/616 | (2006.01) |
| A61K 31/192 | (2006.01) |

(52) U.S. Cl.
CPC ............. *A61K 31/426* (2013.01); *A61K 31/167* (2013.01); *A61K 31/415* (2013.01); *A61K 31/485* (2013.01); *A61K 31/616* (2013.01); *A61K 45/06* (2013.01); *A61K 31/192* (2013.01)

(58) Field of Classification Search
None
See application file for complete search history.

(56) References Cited

U.S. PATENT DOCUMENTS

| | | | |
|---|---|---|---|
| 4,230,717 A | 10/1980 | Lovelace | |
| 4,279,906 A | 7/1981 | Brown et al. | |
| 4,283,408 A | 8/1981 | Hirata et al. | |
| 4,554,276 A | 11/1985 | LaMattina | |
| 4,567,183 A | 1/1986 | Sunshine et al. | |
| 4,599,359 A | 7/1986 | Cooper | |
| 4,683,243 A | 7/1987 | Sunshine et al. | |
| 4,755,532 A | 7/1988 | Sunshine et al. | |
| 4,757,060 A | 7/1988 | Lukacsko et al. | |
| 4,783,465 A | 11/1988 | Sunshine et al. | |
| 4,794,112 A | 12/1988 | Cooper | |
| 4,829,064 A | 5/1989 | Sunshine et al. | |
| 4,871,733 A | 10/1989 | Sunshine et al. | |
| 4,975,426 A | 12/1990 | Sunshine et al. | |
| 4,990,535 A | 2/1991 | Cho et al. | |
| 4,994,327 A | 2/1991 | Kato et al. | |
| 5,009,875 A | 4/1991 | Kelley et al. | |
| 5,037,815 A | 8/1991 | Lukacsko et al. | |
| 5,100,675 A | 3/1992 | Cho | |
| 5,102,902 A | 4/1992 | Mercer | |
| 5,204,118 A | 4/1993 | Goldman et al. | |
| 5,229,137 A | 7/1993 | Wolfe | |
| 5,362,737 A | 11/1994 | Vora et al. | |
| 5,417,980 A | 5/1995 | Goldman et al. | |
| 5,541,212 A | 7/1996 | Bourinbaiar | |
| 5,578,597 A | 11/1996 | Spector et al. | |
| 5,594,276 A | 1/1997 | Murari et al. | |
| 5,718,919 A | 2/1998 | Ruddy et al. | |
| 5,763,422 A | 6/1998 | Lichtenberger et al. | |
| 5,805,580 A | 9/1998 | Vercauteren et al. | |
| 5,955,451 A | 9/1999 | Lichtenberger et al. | |
| 5,993,327 A | 11/1999 | Terril | |
| 6,004,582 A | 12/1999 | Faour et al. | |

(Continued)

FOREIGN PATENT DOCUMENTS

| | | |
|---|---|---|
| EP | 0426479 | 5/1991 |
| EP | 0663839 | 7/1995 |
| WO | 9205783 | 3/1992 |
| WO | 9407541 | 4/1994 |
| WO | 0035298 | 6/2000 |

(Continued)

OTHER PUBLICATIONS

Andersson et al., "Lack of drug-drug interaction between three different non-steroidal anti-inflammatory drugs and omeprazole" Eur. J. Clin. Pharmacol., 1998; 54: 399-404.

(Continued)

*Primary Examiner* — Michael G Hartley
*Assistant Examiner* — Jennifer Lamberski
(74) *Attorney, Agent, or Firm* — Gardner Groff Greenwald & Villanueva, PC

(57) ABSTRACT

Described herein are methods for effectively and accurately measuring a patient response upon administration of one or more drugs to the patient. The methods are more sensitive than current methodologies. Also described herein are compositions comprising an analgesic and a sufficient amount of an antihistamine to enhance the analgesic properties of the analgesic. With respect to these compositions, the methods described herein are useful for evaluating qualities of pain, definite improvement, and one or more bodily functions of a subject afflicted with pain. The compositions described herein are useful in improving the quality of pain in a subject or a bodily function of a subject afflicted with pain or definite improvement of a subject afflicted with pain.

38 Claims, 6 Drawing Sheets

(56) References Cited

U.S. PATENT DOCUMENTS

| | | | |
|---|---|---|---|
| 6,027,746 | A | 2/2000 | Lech |
| 6,130,233 | A | 10/2000 | Woosley et al. |
| 6,146,661 | A | 11/2000 | Hoshino |
| 6,160,020 | A | 12/2000 | Ohannesian et al. |
| 6,187,795 | B1 | 2/2001 | Woosley et al. |
| 6,248,363 | B1 | 6/2001 | Patel et al. |
| 6,261,602 | B1 | 7/2001 | Calanchi et al. |
| 6,270,807 | B1 | 8/2001 | Danielson et al. |
| 6,294,192 | B1 | 9/2001 | Patel et al. |
| 6,303,632 | B1 | 10/2001 | Woosley et al. |
| 6,384,038 | B1 | 5/2002 | Rubin |
| 6,384,054 | B1 | 5/2002 | Woosley et al. |
| 6,395,300 | B1 | 5/2002 | Straub et al. |
| 6,417,184 | B1 | 7/2002 | Ockert |
| 6,471,991 | B2 | 10/2002 | Robinson et al. |
| 6,552,047 | B2 | 4/2003 | Garvey et al. |
| 6,589,551 | B1 | 7/2003 | Jolliffe |
| 6,589,556 | B2 | 7/2003 | Cherukuri |
| 6,596,298 | B2 | 7/2003 | Leung et al. |
| 6,610,667 | B1 | 8/2003 | Dettmar et al. |
| 6,627,235 | B2 | 9/2003 | Vandamme et al. |
| 6,656,482 | B2 | 12/2003 | Mehta et al. |
| 6,663,893 | B2 | 12/2003 | Corbo et al. |
| 6,713,089 | B1 | 3/2004 | Bertelsen et al. |
| 6,773,721 | B1 | 8/2004 | Wong et al. |
| 6,926,907 | B2 | 8/2005 | Plachetka |
| 6,951,871 | B2 | 10/2005 | Aslanian et al. |
| 7,105,505 | B2 | 9/2006 | Zeng et al. |
| 7,186,753 | B1 | 3/2007 | Del Soldato |
| 7,220,735 | B2 | 5/2007 | Ting et al. |
| 7,271,266 | B2 | 9/2007 | Finke et al. |
| 7,300,941 | B2 | 11/2007 | Aslanian et al. |
| 7,323,129 | B2 | 1/2008 | Sowden et al. |
| 7,361,006 | B2 | 4/2008 | Sowden et al. |
| 7,407,669 | B2 | 8/2008 | Leung et al. |
| 7,429,575 | B2 | 9/2008 | Yu et al. |
| 7,482,469 | B2 | 1/2009 | Palin et al. |
| 7,670,612 | B2 | 3/2010 | Miller |
| 7,678,387 | B2 | 3/2010 | Cherukuri |
| 7,678,786 | B2 | 3/2010 | Kuo et al. |
| 7,744,908 | B2 | 6/2010 | Asotra et al. |
| 7,749,533 | B2 | 7/2010 | Fu et al. |
| 7,772,232 | B2 | 8/2010 | Johnson et al. |
| 2003/0130263 | A1 | 7/2003 | Hirsh |
| 2004/0029864 | A1 | 2/2004 | MacMillan |
| 2005/0008690 | A1 | 1/2005 | Miller |
| 2005/0095197 | A1 | 5/2005 | Tuszynski et al. |
| 2005/0163847 | A1 | 7/2005 | Cheng et al. |
| 2006/0034943 | A1 | 2/2006 | Tuszynski |
| 2007/0043096 | A1 | 2/2007 | Tidmarsh et al. |
| 2007/0043097 | A1 | 2/2007 | Tidmarsh et al. |
| 2007/0154542 | A1 | 7/2007 | Tananbaum et al. |
| 2008/0020040 | A1 | 1/2008 | Tidmarsh et al. |
| 2008/0021078 | A1 | 1/2008 | Tidmarsh et al. |
| 2008/0050427 | A1 | 2/2008 | Burch et al. |
| 2008/0063706 | A1 | 3/2008 | Tidmarsh et al. |
| 2009/0142393 | A1 | 6/2009 | Xu et al. |
| 2009/0264484 | A1 | 10/2009 | Tidmarsh et al. |
| 2009/0275622 | A1 | 11/2009 | Linga et al. |
| 2010/0227854 | A1 | 9/2010 | Tananbaum et al. |
| 2010/0297224 | A1 | 11/2010 | Tidmarsh et al. |

FOREIGN PATENT DOCUMENTS

| | | |
|---|---|---|
| WO | 0143722 | 6/2001 |
| WO | 03026627 | 4/2003 |
| WO | 2005063219 | 7/2005 |
| WO | 2006052856 | 5/2006 |
| WO | 2007072503 | 6/2007 |

OTHER PUBLICATIONS

Bacracheva et al. Effect of cimetidine on the pharmacokinetics of the metabolites of metamizol. Int. J. Clin. Pharmacol. Ther. 1997; 35(7): 275-281. (abstract only).

Birk et al. "A fixed dose combination of ibuprofen and famotidine," Expert Opinion, 2009, 1385-91. Informa UK Ltd.

Bluhm et al., Potentiation of Opoid Anagesia by H1 and H2 Antagonists, Life Sciences, vol. 31, Issues 12-13, Sep. 1982, pp. 1229-1232.

Busch et al. Interaction of meloxicam with cimetidine, Maalox, or aspirin. J. Clin. Pharmacol. 1996; 36(1): 79-84.

Dammann et al. Differential effects of misoprostil and ranitidine on the pharmacokinetics of diclofenac and gastrointestinal symptoms. Br. J. Clin. Pharmacol. 1993; 36(4): 345-349.

Delhotal-Landes et al. Pharmacokinetic interations between NSAIDs (indomethacin or sulindac) and H2-receptor antagonists (cimetidine or ranitidine) in human volunteers. Clin. Pharmacol. Ther. 1988; 44 (4): 442-452.

Dixon et al. A lack of pharmacokinetic interaction between ranitidine and piroxicam. Eur. J. Clin. Pharmacol. 1990; 39(6): 583-586.

Evans et al., "Lack of effect of cimetidine on the pharmacokinetics of R-(–) and S-(+) ibuprofen" Br. J. Clin. Pharmacol., 1989; 28: 143-149.

Forsyth et al., Do Nizatidine and Cimetidine Interact with Ibuprofen? 1988, Eur. J. Clin. Pharmacol., 35: 85-88.

Hough et al. "Novel Qualitative Structure-Activity Relationships for the Antinociceptive Actions of H2 Antagonists, H3 Antagonists and Derivatives," The Journal of Pharmacology and Experimental Therapeutics, 1997, 1534-43.

Kendall et al., "Coadministration of misoprostol or ranitidine with indomethacin: effects on pharmacokinetics, abdominal symptoms and bowel habit" Aliment Pharmacol. Ther. 1992; 6;437-446.

Laska et al. "The correlation between blood levels of ibuprofen and clinical analgesic response," Clinical Pharmacology and Therapeutics, 1986, 1-7. (abstract only).

Leucuta et al. No effect of short term ranitidine on diclofenac pharmacokinetics. Rom. J. Gastroenterol. 2004; 13(4): 306-308.

Milligan et al. The consequences of H2 receptor antagonist-piroxicam coadministration in patients with joint disorders. Eur. J. Clin. Pharmacol. 1993: 45(6): 507-512.

Naproxen Report, 1983, 8pp.

Ochs et al . "Interaction of ibuprofen with the H-2 receptor antagonists ranitidine and cimetidine," Clinical Pharmacology and Therapeutics, 1985, 648-51.

Parrott et al. "Influence of cimetidine on the disposition of ibuprofen in the rat," Research Communications in Chemical Pathology and Pharmacology, 1984, 369-80. (abstract only).

Raffa "Antihistamines as analgesics," Journal of Clinical Pharmacology and Therapeutics, 2001, 81-5.

Ravic et al. A pharmacokinetic interaction between cimetidine or ranitidine and lornoxicam. Postgrad. Med. J. 1993; 69: 865-866.

Rumore et al., "Clinical Efficacy of Antihistaminics as Analgesics," Pain, 25, 1986, pp. 7-22.

Said et al. Influence of cimetidine on the pharmacokinetics of piroxicam in rat and man. Arzneimittelforschung 1989; 39(7): 790-792. (abstract only).

Santiago-Palma et al. "Diphenhyramine as an Analgesic Adjuvant in Refractory Cancer Pain", Journal of Pain and Symptom Management, 2001, vol. 22., No. 2, pp. 699-703, Elsevier, New York.

Schachtel et al., 1984, "Rating Scales for Analgesics in Sore Throat," Clin. Pharmacaol. & Therapeut., 36(2): 151-156.

Schachtel et al., 1988, "Sore Throat Pain in the Evaluation of Mild Analgesics," Clin. Pharmacol. & Therapeut., 44 (6): 704-711.

Schachtel et al., 1993, "A placebo-controlled model for assaying systemic analgesics in children," Clin. Trials & Therapeut., 593-601.

Schachtel et al., 2002, "Demonstration of dose response of flurbiprofen lozenges with the sore throat pain model," Clin. Pharmacol. & Therapeut. 71:375-380.

Schachtel et al., 2007, "Utility and Sensitivity of the Sore Throat Pain Model: Results of a Randomized Controlled Trial on the COX-2 Selective Inhibitor Valdecoxib," J. Clin. Pharmacol 47:860-870. (Originally published online May 24, 2007).

Schachtel, 1991, "Sore Throat Pain," Advances in Pain Research and Therapy, vol. 18, ed. M. Max, R. Portenoy, & E. Laska, New York: Raven Press, Ltd., pp. 393-407.

(56) References Cited

OTHER PUBLICATIONS

Shamburek et al, "Control of gastric acid secretion. Histamine H2-receptor antagonists and H+K(+)-ATPase inhibitors." Medical College of Virginia, Richmond, Gastroenterol Clinic North America, Sep. 1992, 21(3):527-50. (abstract only).

Singh et al., "Gastrointestinal Tract Complications of Nonsteroidal Anti-inflammatory Drug Treatment in Rheumatoid Arthritis" Arch. Intern. Med., 1996; 156: 1530-1536.

Small et al., "Influence of H2-receptor antagonists on the disposition of flurbiprofen enantiomers" J. Clin. Pharmacol. 1990; 30: 660-664.

Verbeeck et al. "Single and multiple dose pharmacokinetics of enteric coated ketoprofen: effect of cimetidine" Eur. J. Clin. Pharmacol. 1988; 35: 521-527.

Vimovo: (naproxen/esomeprazole magnesium) Delayed-released tablets, Pharmacy & Therapeutics, 2010, 35(9 Section 2): 2-4.

Vovk et al. "The modification of the pharmacokinetics and analgesic effect of naproxen by cimetidine, phenobarbital and thiamine diphosphate," Experiments in Clinical Pharmacology, 1996, 35-7. (abstract only).

Vree et al. The effects of cimetidine, ranitidine, and famotidine on the single-dose pharmacokinetics of naproxen and its metabolites in humans. Int. J. Clin. Pharmacol. Ther. Toxicol. 1993; 31(12): 597-601. (abstract only).

Vree et al. The pharmacokinetics of naproxen, its metabolite O-desmethylnaproxen, and their acyl glucuronides in humans. Effect of cimetidine. Br. J. Clin. Pharmacol. 1993; 35(5): 467-472.

Australian Examination Report for application No. 2009204360 dated Apr. 26, 2013.

First Examination Report dated Feb. 22, 2011 for New Zealand application No. 587202.

Second Examination Report dated Jun. 13, 2012 for New Zealand application No. 587202.

European Search Report dated Dec. 8, 2011 for EP application No. 09700489.9.

International Search Report and Combination Written Opinion in re PCT/US2009/30079, mailed Feb. 26, 2009.

USE OF ANALGESIC POTENTIATING COMPOUNDS TO POTENTIATE THE ANALGESIC PROPERTIES OF AN ANALGESIC COMPOUND

CROSS REFERENCE TO RELATED APPLICATIONS

This application is a continuation application of U.S. application Ser. No. 12/811,528, filed on Sep. 8, 2010, which is a U.S. national phase application under 35 USC 371 of international application number PCT/US2009/030079, filed Jan. 5, 2009, which claims priority to U.S. provisional application Ser. No. 61/019,025, filed Jan. 4, 2008, which are hereby incorporated herein by reference in their entirety for all purposes.

BACKGROUND

When a patient is administered a drug, the patient generally produces a response that is perceptible to the patient. For example, when a subject is experiencing pain, the subject will take a medication to relieve the pain symptoms. By effectively detecting and measuring the patient response, information regarding the effectiveness of the drug can be obtained and evaluated. An example of this includes analgesic potentiation. "Analgesic potentiation" is a type of pharmacologic activity that occurs when greater analgesic effectiveness is measured in patients treated with an analgesic drug combined with a non-analgesic ingredient than in patients treated with the analgesic drug alone. There are many reasons for the potentiation of an analgesic. For example, it would be desirable to enhance the clinical outcome for the patient (i.e., analgesic effectiveness). It would also be desirable to reduce the dosage of the analgesic (i.e., "optimal dose") that is administered in view of possible side effects exhibited by the same or higher dose of the analgesic (i.e., "optimal analgesia," a reduction of the risk:benefit ratio). It would also be desirable to provide greater pain relief or faster onset of pain relief. It would also be desirable to provide a longer duration, which results in less frequent dosing and better compliance. Finally, if the analgesic can improve one or more qualities of pain or one or more bodily functions of the patient or provide definite improvement of the patient, which will be discussed in greater detail below, these would be added benefits.

The measurement instruments for these overall effects are standard methods for determining general patient response such as analgesic activity. In the evaluation of analgesic potentiation, for example, clinical investigators by convention utilize these methods to demonstrate, to a statistically significant degree, that a combination of drugs provides "greater reduction in pain intensity" and "more pain relief" than the single-ingredient analgesic. However, conventional methods may not be able to demonstrate that a combination of the analgesic with another drug provides analgesic effectiveness to a greater extent than the analgesic alone. Measuring these conventional overall endpoints (i.e., "pain" and "relief") may obscure specific clinical benefits that are meaningful to the patient and analgesic potentiation due to the presence of an additional drug or ingredient used in combination with the analgesic.

Thus, what are needed are methods for increasing or enhancing the measurement of patient responses. These methods could be used to demonstrate what is otherwise non-demonstrable using conventional methods.

SUMMARY OF EMBODIMENTS

Described herein are methods for effectively and accurately measuring a patient response upon administration of one or more drugs to the patient. The methods are more sensitive than current methodologies. Also described herein are compositions comprising an analgesic and a sufficient amount of an antihistamine to enhance the analgesic properties of the analgesic. With respect to theses compositions, the methods described herein are useful for evaluating qualities of pain, definite improvement, and one or more bodily functions of a subject afflicted with pain. The compositions described herein are useful in improving the quality of pain in a subject or a bodily function of a subject afflicted with pain or definite improvement of a subject afflicted with pain.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
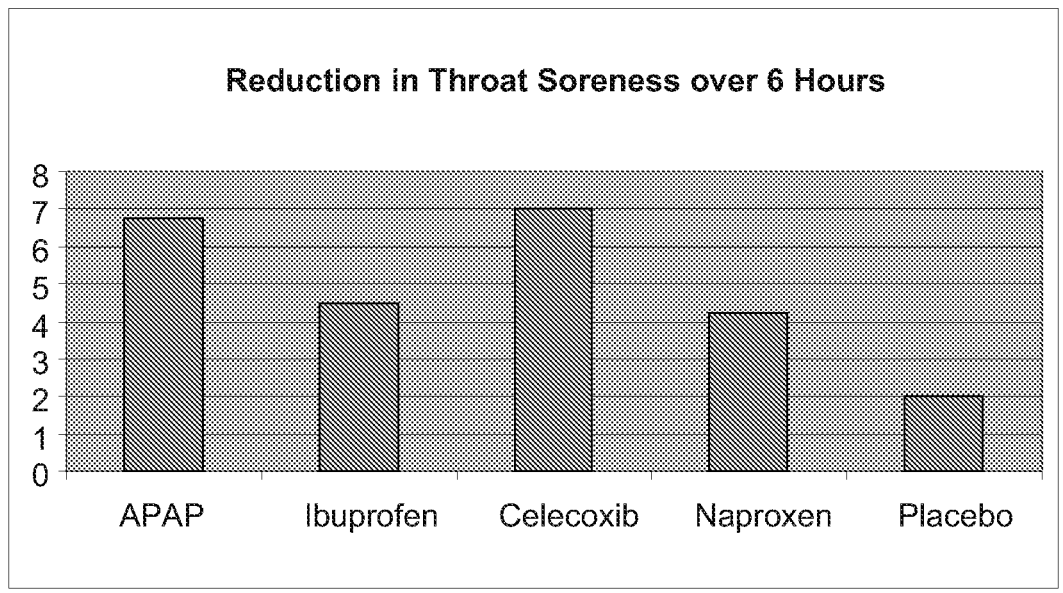
FIG. 1 shows the reduction in throat soreness over 6 hours of several analgesics (acetaminophen 500 mg (APAP), ibuprofen 200 mg, celecoxib 200 mg, naproxen sodium 220 mg) and placebo.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

The term "comparative agent" as used herein is any agent that is used to compare or evaluate the ability of an antihistamine to potentiate the analgesic properties of an analgesic. For example, the comparative agent can be a placebo, another drug, or a combination of drugs. Thus, the effects of a known analgesic can be evaluated and compared to that of the comparative agent, confirming the pharmacologic activity of the analgesic and thus validating the method itself. For example, when a patient is administered an analgesic and an antihistamine, the comparative agent is the administration of just the analgesic to the patient. In this example, the effects of the antihistamine on the analgesic can be evaluated and compared to that of the analgesic alone, thus identifying any additional pharmacologic activity provided by the antihistamine ("analgesic potentiation").

Described herein are methods for evaluating a subject's response when administered one or more drugs. In one aspect, the method includes:
a. obtaining a baseline of one or more symptoms in the subject;
b. requiring a pre-determined minimal intensity level of one or more symptoms;
c. administering one or more drugs to the subject that will elicit one or more responses perceptible to the subject;
d. evaluating one or more responses in the subject and comparing them to the baseline in step (a); and
e. comparing the response in step (d) in the subject with a response of the subject who was administered a comparative agent.

In another aspect, a method for evaluating definite improvement of a subject afflicted with one or more adverse symptoms after the administration of one or more drugs to the subject includes:
a. administering one or more drugs to the subject;
b. requiring a pre-determined minimal intensity level of one or more symptoms;
c. evaluating whether or not there is definite improvement of the adverse symptoms after administration of the drug or drugs to the subject; and
d. comparing the response in step (c) in the subject with a response of the subject who was administered a comparative agent.

In general, the methods described herein are more sensitive with respect to detecting and measuring a patient's response to one or more drugs. The methods can be used in a variety of therapeutic areas exhibiting adverse symptoms including, but not limited to, gastrointestinal (e.g., for patients with heartburn, abdominal pain, nausea and vomiting); respiratory (e.g., for patients with asthma, chronic obstructive lung disease, cough, nasal congestion); musculoskeletal (e.g., for patients with osteoarthritis, sprains, rheumatoid arthritis, spinal disorders); dermatological (e.g., for patients with eczema, hives, psoriasis, sun sensitivity); psychiatric (e.g., for patients with depression, anxiety, sleep disorders); CNS (e.g., for patients with tension headache, migraine headache, light sensitivity); and allergic disorders (e.g., for patients with seasonal allergic rhinitis, perennial allergic rhinitis).

In one aspect, the methods described herein measure a definite improvement after the administration of the drug(s). The phrase "definite improvement" is defined herein as the ability of the drug to elicit a response followed by subsequent questioning to evaluate whether or not the subject's condition has improved. In general, "definite improvement" can be evaluated by directly asking the subject certain questions that will prompt the subject to precisely consider whether or not the subject's condition has unequivocally improved such that the response is significantly perceptible to the subject and is so reported by the subject. In one aspect, the degree or amount of the response can be measured using a multipoint scale, which can vary from little to no improvement to certain improvement. "Definite improvement" is greater than 50% improvement to 100% improvement as perceived and reported by the patient on this scale. In another aspect, "definite improvement" is at or lower than a response level perceived by the subject on one or more individual rating scales.

For example, patients with asthma may be able to report "definite improvement" because several symptoms have, in subtle ways, improved, or these patients may be able to report less chest tightness, a sensory quality of asthma, even though, in clinical trials, they may not report "relief" of asthma symptoms. Patients with osteoarthritis may report less joint "stiffness," a sensory quality of arthritic status, even though they may not report "relief" of their disease in clinical studies. Patients with hives may report an ability to move an effected body part more freely (i.e., function) even though they may not report "relief" of their condition in research trials. For each example, specific "patient-oriented" endpoints may reveal the actual clinical benefits. Each specific endpoint of patient dis-ease (rather than physician-diagnosed disease) may reveal the actual clinical benefit to the patient.

Examples of definite improvement associated with pain include, but are not limited to, headache, backache, sinusitis, earache, cough discomfort, sinus pain associated with nasal congestion, difficulty breathing, toothache, sprained ankle, muscle strain, sprained or torn ligaments, and bursitis.

The methods described herein are useful in evaluating if a drug (alone or in combination with other drugs) is useful in eliciting a desirable response. For example, the response elicited by the patient when administered a drug can be compared to the patient's response when the subject is administered a comparative agent as defined above.

In one aspect, described herein is a method for evaluating one or more qualities of pain in a subject afflicted with pain, comprising:
(a) obtaining a baseline of one or more qualities of pain in the subject;
(b) requiring a pre-determined minimal intensity level of one or more qualities of pain;
(c) administering a composition comprising an analgesic and an antihistamine to the subject;
(d) evaluating one or more qualities of pain in the subject and comparing them to the baseline in step (a); and
(e) comparing the response in step (d) to the response in the subject administered just the analgesic.

In another aspect, described herein is a method for evaluating one or more bodily functions of a subject afflicted with pain, comprising:

(a) obtaining a baseline of one or more bodily functions of the subject experiencing pain;
(b) requiring a pre-determined minimal intensity level of one or more bodily functions;
(c) administering a composition comprising an analgesic and an antihistamine to the subject;
(d) evaluating one or more bodily functions in the subject and comparing them to the baseline in step (a); and
(e) comparing the response in step (d) to the response in the subject administered just the analgesic.

In a further aspect, described herein is a method for evaluating definite improvement of a subject afflicted with pain, comprising:
(a) obtaining a baseline of one or more symptoms in the subject;
(b) requiring a pre-determined minimal intensity level of one or more symptoms;
(c) administering a composition comprising an analgesic and an antihistamine to the subject;
(d) evaluating whether there is definite improvement in the subject of one or more symptoms; and
(e) comparing the response in step (d) to the response in the subject administered just the analgesic.

The methods described herein use rating scales that measure changes in the words which patients actually use to describe their discomfort and whether or not they achieved definite improvement on each scale, instead of traditional analgesic methods (i.e., measuring differences in overall pain intensity or relief). In certain aspects, the methods described herein for evaluating pain in a patient and the effect of the combination of an analgesic and antihistamine utilize non-standard methods:
1. to measure qualities of pain clinically relevant to patients with the pain-producing condition;
2. to measure function(s) clinically relevant to patients with the pain-producing condition;
3. to examine the effect of each combination drug upon qualities of pain in this sample pain model;
4. to examine the effect of each combination drug on function(s); and
5. to examine if a patient was "definitely improved."

The methods described herein represent a progression beyond conventional analgesic measurement instruments and attempt to measure "patient-oriented" clinical effects in order to determine analgesic potentiation, i.e., if sample antihistamine/analgesic combinations deliver more pronounced analgesia compared to the respective single-ingredient analgesics. Measuring conventional endpoints (e.g., "pain" and "relief") may obscure the identification of clinical benefits.

The type of pain can be acute or chronic. The source of the pain can vary and includes, but is not limited to, renal colic, colic, gallstone pain, ulcer pain, sinus pain, migraine headache, cluster ("histamine") headache, muscle contraction headache, osteoarthritis, rheumatoid arthritis, gouty arthritis, other arthritides, ligamentous sprain, bursitis, soft tissue injuries (e.g., torn subpatellar meniscus or ligament), skeletal muscle (e.g., low back pain, muscle ache, muscular contusion, muscular strain, muscle spasm, neck spasm/pain, etc.). In other aspects, the source of pain can be post-operative (e.g., following abdominal surgery, thoracic surgery, neurosurgery, orthopedic surgery, podiatric surgery, anorectal surgery, urologic surgery, gynecologic surgery, episiotomy, oral surgery, head and neck surgery, plastic surgery, etc.). In other aspects, the source of pain can be the result of infection (e.g., a subject experiencing pain as a result of sinusitis, laryngitis, pharyngitis, otitis media, cellulitis, abscess, meningitis, conjunctivitis, osteoarthritis, osteomyelitis, etc.), In other aspects, the source of pain can be the result of vascular insufficiency (e.g., a subject experiencing pain as a result of peripheral vascular disease or coronary artery disease). In other aspects, the source of pain can be the result of a previous treatment (e.g., a subject experiencing pain as a result of receiving chemotherapy or radiation) or the result of cancer (e.g., primary carcinoma or metastatic bone pain). Each type of pain presents "patient-oriented" clinical effects that can be measured by the methods described herein and/or improved by the compositions described herein.

In one aspect, the compositions described herein improve one or more qualities of pain in a subject. The phrase "improve the quality of pain" is defined herein as the ability of the composition to reduce the subject's sensation of a particular quality or qualities of pain. For example, when a subject is experiencing a sore throat, the subject may experience a hot, scratchy, raw, raspy, dry, tight, swollen, or burning sensation or consider the sensation annoying or irritating. These are examples of qualities of pain associated with a sore throat (as caused, e.g., by pharyngitis, seasonal allergic rhinitis ("hayfever"), perennial allergic rhinitis). Other examples of qualities of pain associated with other painful conditions include, but are not limited to, headache, backache, sinusitis, earache, toothache, sprained ankle, joint pain, arthritis, bursitis, vascular insufficiency, cancer-related pain, post-operative pain.

In other aspects, the compositions described herein improve one or more bodily functions of a subject afflicted with pain. The phrase "improve one or more bodily functions" is defined herein as the ability of the composition to improve a bodily function of a subject that is debilitated or weakened as a result of pain experienced by the subject. For example, when a subject is experiencing a sore throat, the subject may have trouble swallowing or difficulty talking, where swallowing and talking are the bodily functions. These are examples of bodily functions associated with a sore throat (as caused, e.g., by tonsillopharyngitis, oral mucositis). Other examples of bodily functions associated with other painful conditions include, but are not limited to, headache, backache, sinusitis, earache, toothache, sprained ankle, joint pain, arthritis, bursitis, vascular insufficiency, cancer-related pain, post-operative pain.

In another aspect, the compositions described herein can be shown directly to provide definite improvement. The phrase "definite improvement" is defined herein as the ability of the composition to reduce the subject's sensation of a particular quality(ies) of pain or bodily function(s) at least to his/her own level defining successful treatment. Grading a reduction in pain intensity may be inadequate to detect improvement in physical status. Rather than infer a change in status by subtracting one "pain" rating from another, as is commonly performed in clinical trials, subjects can define their own criterion of successful treatment as a direct indicator of therapeutic efficacy. For example, one subject with a "swollen" throat may rate it "10" on a 0-10 scale: for him/her, reducing this sensation to "6" or below may be the clear measure of whether or not a medication is "working." For another subject, with a "7" rating of throat swelling, reducing this sensation to "3" is inadequate, only a rating of "2" or below means "definite improvement." Other examples apply to other qualities of pain or bodily functions. Each patient's "definite improvement level" on a rating scale can be used to identify a successful treatment response, or not. Thus response rates of patients treated with a drug can be compared to those of patients treated with placebo, identifying therapeutic efficacy.

The evaluation methods described herein provide numerous advantages over existing techniques. First, it is possible to detect wide differences (e.g., ranging from 20% to over 100%) between some antihistamine/analgesic combinations and the corresponding single-ingredient analgesic. Additionally, the methods are more sensitive with respect to differentiating the effects of different combinations of analgesic and antihistamine. For example, unlike the requirement for an entry level≥7 for the conventional scale Throat Soreness Scale (TSS), there are no admission criteria for using the methods described herein, which ranged from 0 to 10 at baseline. Despite this "all-comer" study sample, the methods described herein were used by the patients in each treatment group to measure impressive effects and identify clear drug-vs.-placebo and between-drug differences. Due to greater sensitivity, the methods described herein may require fewer patients in a clinical trial than with a conventional rating scale and be capable of discerning clinical effects better.

In one aspect, the composition for improving. (e.g., providing definite improvement of) at least one quality of pain and/or at least one bodily function comprises an analgesic and a sufficient amount of an antihistamine to enhance the analgesic properties of the analgesic. In general, the analgesic and antihistamine are FDA-approved chemical compounds.

In one aspect, the analgesic comprises a non-opioid. Examples of non-opioids include, but are not limited to, acetaminophen, aspirin, ibuprofen, naproxen sodium, naproxen, indomethacin, flurbiprofen, ketoprofen, lornoxicam, meloxicam, piroxicam, oxaprozin, etodolac, ketorolac, nabumetone, or other nonselective nonsteroidal anti-inflammatory drugs (NSAIDs), selective COX-2 inhibitors (e.g., celecoxib, rofecoxib, valdecoxib, parecoxib, etoricoxib, CS-502, JTE-522, L-745,337, and NS398), NDMA-inhibitors, or any combination thereof, optionally with other components such as, for example, caffeine or other analgesic adjuvant(s), with or without other ingredients for non-analgesic indications (e.g., "cough-cold products" which may contain, in varying combinations, an analgesic/antipyretic, an antihistamine, an antitussive, a decongestant, an expectorant, etc.). Alternatively, the analgesic comprises an opioid including, but not limited to, morphine, codeine, buprenorphine, hydrocodone, oxycodone, fentanyl, tramadol, pentazocine, meperidine, or any combination thereof with or without caffeine or other analgesic adjuvant(s), optionally with other ingredients for non-analgesic indications (e.g., "cough-cold products," which may contain, in varying combinations, an analgesic/antipyretic, an antihistamine, an antitussive, a decongestant, an expectorant, etc.).

Pharmaceutically acceptable salts of the analgesic can be used herein. For example, suitable pharmaceutically acceptable salts of ibuprofen include ibuprofen lysinate, dexibuprofen lysinate, and sodium and potassium salts of ibuprofen. Other examples of pharmaceutically acceptable salts of ibuprofen include salts with alkaline earth metals, such as magnesium, aluminum, iron, zinc, copper, nickel or cobalt, and amino acid salts, particularly the basic amino acid salts such as lysine or arginine. Examples of suitable forms of ibuprofen include, but are not limited to racemic and individual purified forms of (S) ibuprofen and (R)-ibuprofen isomers, including (S)-ibuprofen-(S)-lysine, (S)-ibuprofen-(R)-lysine, (R)-ibuprofen-(S)-lysine and (R)-ibuprofen-(R)-lysine and combinations thereof.

A variety of different antihistamines can be used herein. In one aspect, the antihistamine comprises a sedating $H_1$ antihistamine, a non-sedating $H_1$-antihistamine, a $H_2$-antihistamine, an experimental $H_3$- and $H_4$-receptor antagonist, or any combination thereof. Examples of sedating $H_1$-antihistamines include, but are not limited to, diphenhydramine, hydroxyzine, any salt or isomer thereof, or a combination thereof. Useful non-sedating $H_1$-antihistamines include, but are not limited to, astemizole, azatadine, azelastine, cetirizine, ebastine, fexofenidine, ketotifen, lodoxamide, loratadine, desloratadine, levocabastine, mequitazine, oxatomide, setastine, tazifylline, and terfenadine, any salt or isomer thereof, or any combination thereof. Examples of $H_2$-antihistamines include, but are not limited to, nizatidine, ranitidine, famotidine, cimetidine, roxatidine, lafutidine, ebrotidine, burimamide, metiamide, tiotidine, oxmetidine, pabutidine, loxtidine, any salt or isomer thereof, or any combination thereof. Examples of $H_3$-antihistamines include, but are not limited to, A-349,821, ABT-239, ciproxifan, clobenpropit, or thioperamide, any salt or isomer thereof, or any combination thereof. Examples of $H_4$-antihistamines include, but are not limited to, thioperamide, JNJ 7777120, VUF-6002, any salt or isomer thereof, or any combination thereof.

The amounts of analgesic and antihistamine can vary depending upon the selection of the analgesic and antihistamine, the type of pain experienced by the subject, the route and means of drug administration, and the frequency of dosing. In one aspect, the analgesic is a single dosage from 0.1 mg to 1,500 mg and the antihistamine is a single dosage from 0.1 mg to 1 g. In another aspect, the amount of analgesic is 0.1 mg, 0.5 mg, 1 mg, 5 mg, 10 mg, 20 mg, 30 mg, 40 mg, 50 mg, 60 mg, 70 mg, 80 mg, 90 mg, 100 mg, 200 mg, 300 mg, 400 mg, 500 mg, 600 mg, 700 mg, 800 mg, 900 mg, 1,000 mg, 1,100 mg, 1,200 mg, 1,300 mg, 1,400 mg, or 1,500 mg, where any value can form a lower or upper endpoint of a range. In a further aspect, the amount of antihistamine is 0.1 mg, 0.5 mg, 1 mg, 5 mg, 10 mg, 50 mg, 100 mg, 150 mg, 200 mg, 250 mg, 300 mg, 350 mg, 400 mg, 450 mg, 500 mg, 600 mg, 700 mg, 800 mg, 900 mg, or 1,000 mg, where any value can form a lower or upper endpoint of a range. In another aspect, the weight ratio of analgesic to antihistamine is 20:1, 18:1, 16:1, 14:1, 12:1, 10:1, 8:1, 6:1, 4:1, 2:1, or 1:1.

The analgesic and antihistamine can be formulated into a variety of pharmaceutical compositions. The pharmaceutical compositions can be prepared using techniques known in the art. In one aspect, the composition is prepared by admixing the analgesic and the antihistamine with a pharmaceutically-acceptable carrier. Alternatively, the analgesic and antihistamine are formulated such that the analgesic and the antihistamine are in separate delivery devices. In this aspect, the analgesic and the antihistamine can be administered to the subject separately and independently (e.g., to achieve immediate-release or delayed-release responses by and to one or both component drugs). In one aspect, the antihistamine can be administered first followed by the administration of the analgesic. For example, when the antihistamine is nizatidine and the analgesic is ibuprofen, the nizatidine can be administered first followed by the administration of ibuprofen. Not wishing to be bound by theory, when the nizatidine is an immediate-release preparation (e.g., a powder), the dissolution and bioavailability of the nizatidine is increased when compared to the slower dissolution and bioavailability of ibuprofen in a compressed tablet.

The analgesic and antihistamine can be formulated in any excipient the subject can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity-enhancing agents, such as sodium carboxymethylcellulose, sorbitol, or dextran.

The pharmaceutical compositions can include other components that are non-analgesics and non-antihistamines. For example, the pharmaceutical compositions can contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In one aspect, the compounds described herein are admixed with a non-FDA approved delivery device such as, for example, sunscreen or a nutraceutical. In other aspects, the pharmaceutical compositions can also include one or more active ingredients such as antimicrobial agents, antiinflammatory agents, anesthetics, decongestants, antitussives, expectorants, antipyretics, and the like.

The pharmaceutical compositions can be administered in a number of ways. In one aspect, the compositions can be administered orally as a tablet or pill. The analgesic and antihistamine can be formulated with a variety of suitable carriers, excipients, and diluents known in the art. Examples of such materials include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents.

The compositions of the invention may be formulated so as to provide quick release, sustained release, or delayed release of the analgesic and/or antihistamine after administration to the subject. Different pharmaceutic formulations and different processing techniques may be employed to alter the pharmacokinetic characteristics of the compositions, including, without limitation, time to maximum concentration, maximum concentration, area under the curve, etc. In one aspect, the analgesic and antihistamine can be formulated with biodegradable polymers such as, for example, polylactide, polyglycolide, or polylactide-co-glycolide, where the analgesic and antihistamine are incorporated in a polymeric matrix. By varying the amount and molecular weight of the biodegradable polymer, it is possible to control the rate of release of the analgesic and the antihistamine. In another aspect, the tablet or pill can be formulated such that the tablet or pill contains two or more layers of varying disintegration and dissolution rates. In other aspects, the compositions can be encapsulated in order to control the rate of release of the analgesic and antihistamine With respect to any of the oral formulations described above, the analgesic and antihistamine can be formulated into one tablet or pill or, in the alternative, the analgesic and antihistamine can be formulated into separate tablets or capsules.

The compositions described herein can be administered topically (including ophthalmically, vaginally, rectally, buccally, intranasally). Formulations for topical administration can include ointments, lotions, creams, gels, patches, drops, suppositories, sprays, liquids and powders. Alternatively, the compositions described herein can be prepared as sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Provided below is a representative study for evaluating the qualities of pain and bodily functions that are reduced and definite improvement when a subject is experiencing pain using the compositions and methods described herein. Specific methodology and techniques are provided in the Examples.

Treatment Schedule

According to a computer-generated randomization code, the following treatments will be assigned under double-blind conditions:
1. Acetaminophen 500 mg
2. Acetaminophen 500 mg+cetirizine 20 mg
3. Celecoxib 200 mg
4. Celecoxib 200 mg+cetirizine 20 mg
5. Naproxen sodium 220 mg
6. Naproxen sodium 220 mg+loratadine 20 mg
7. Ibuprofen 200 mg
8. Ibuprofen 200 mg+loratadine 20 mg
9. Ibuprofen 200 mg+hydroxyzine 50 mg
10. Ibuprofen 200 mg+nizatidine 150 mg
11. Placebo Baseline Characteristics
1. Onset of sore throat in past 5 days
2. Tonsillo-Pharyngitis Assessment (TPA)≥5
3. Throat Soreness Scale≥7
4. No mouth-breathing or throat discomfort with coughing
5. May have symptoms of allergic rhinitis, but no use of antihistamines on a regular basis
6. No medical contraindications (e.g., relevant drug allergies or diseases)

Measurement Instruments
1. Throat Soreness Scale* [evaluative quality-of-pain scale]
2. Swollen Throat Scale* [sensory quality-of-pain scale]
3. Difficulty Swallowing Scale** [function scale]
4. Difficulty Talking Scale** [function scale]
5. Quality-of-Pain Scales* [measuring other sensory qualities of pain (hot, scratchy, raw, raspy, tight, dry, burning), affective qualities of pain (irritating, annoying), and another evaluative quality of pain (it hurts)]
6. Definite Improvement Assessment [transitional scale]
7. Definite Improvement Level [nominal scale]

Study Procedures
1. Screening, Consent process
2. Brief Medical History, URTI Symptoms and Sore Throat History (duration, treatments)
3. Temperature (oral), pulse, respiratory rate
4. Respiratory (lungs and nose) examination and TPA
5. Urine pregnancy test on all eligible female patients
6. Baseline evaluations (throat soreness, swollen throat, difficulty swallowing, difficulty talking, qualities of pain) under the supervision of the Study Nurse
7. Qualifying patients are administered the randomly assigned identically-appearing study medications (prepared, packaged, and coded by independent pharmacist) with a full glass of water
8. Post-treatment evaluations of throat soreness, swollen throat, difficulty swallowing, and improvement under the supervision of the Study Nurse at 15-minute intervals over 2 hours
9. Post-treatment evaluations of difficulty talking and qualities of pain under the supervision of the Study Nurse at 1 hour and 2 hours 10. After these 2-hour evaluations: routine clinic procedures (e.g., Strep Test, Throat Culture, Mono Test). Treatment (e.g., topical/systemic analgesics, antibiotic) initiated at physician's discretion (e.g., after Throat Culture results). After these procedures: discharge from clinic with instructions how to use Home Diary.
11. Post-treatment evaluations of throat soreness, swollen throat, difficulty swallowing, difficulty talking, and improvement at 3, 4, 5, and 6 hours.
12. Post-treatment evaluations of qualities of pain at 6 hours.
13. Follow-up visit within 5 days to determine definite improvement levels for each scale, review Diary and evaluate any side effects. Discharge from study, routine care and follow-up per standard clinic protocol.

Endpoints

1. Primary Endpoint: Difference in difficulty swallowing over 6 hours
2. Secondary Endpoints:
   a. Difference in Quality-of-Pain Index* over 6 hours
   b. Difference in Throat Function Index** over 6 hours
   c. Difference in throat soreness over 6 hours
   d. Difference in throat swelling over 6 hours
   e. Difference in relatively severe (baseline>7) qualities of pain
   f. Difference in relatively severe sensory qualities of pain
   g. Difference in most bothersome quality(ies) of pain***
   h. Differences in difficulty swallowing at individual time points
   i. Differences in relatively severe difficulty talking
   j. Differences in throat soreness at individual time points
   k. Differences in throat swelling at individual time points
   l. Percentage of patients with definite improvement
   m. Total improvement over 6 hours
   n. Improvement at individual time points In certain aspects, for each treatment group, improvement and differences from Baseline may be reported as medians and percentage differences.

*Throat soreness (an evaluative quality of pain), throat swelling (a sensory quality of pain), and the other 10 qualities of throat pain comprise the 0-to-120 point Quality-of-Pain Index.
**Difficulty Swallowing and Difficulty Talking comprise the 0-to-20 point Throat Function Index.
***The most bothersome quality of pain has the highest Baseline score. Qualities that have the same highest Baseline score (i.e., ties) may be examined, too. "Most bothersome quality(ies)" will be analyzed separately and as a group since these are the most bothersome qualities of pain from the patient's point of view (in keeping with the guiding principle and focus of this research, "patient-oriented" clinical effects).

Additional Compositions and Tests
1. Ibuprofen 200 mg vs. placebo
2. Ibuprofen 200 mg+loratadine 20 mg vs. ibuprofen 200 mg
3. Ibuprofen 200 mg+hydroxyzine 50 mg vs. ibuprofen 200 mg
4. Ibuprofen 200 mg+nizatidine 150 mg vs. ibuprofen 200 mg
5. Acetaminophen 500 mg vs. placebo
6 Acetaminophen 500 mg+cetirizine 20 mg vs. acetaminophen 500 mg
7. Celecoxib 200 mg vs. placebo
8. Celecoxib 200 mg+cetirizine 20 mg vs. celecoxib 200 mg
9. Naproxen sodium 220 mg vs. placebo
10. Naproxen sodium 220 mg+loratadine 20 mg vs. naproxen sodium 220 mg
11. Each combination vs. placebo at individual time points
12. Sensitivity appraisals and internal validation of measurements on the Quality-of Pain Index, the Throat Function Index, and the Definite Improvement Assessment by examining the comparison of ibuprofen 200 mg (the positive control) with placebo. External validation of measurements by examining the comparison of ibuprofen 200 mg (the positive control) with placebo and correlating these measurements with those from the Throat Soreness Scale, a validated scale.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventor regards as his invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Study Design

A randomized, double-blind, placebo-controlled single-dose study was performed. In order to be eligible for the study, patients were required to have a history of an acute sore throat and physical evidence of pharyngitis. A total of 99 patients who met pre-specified inclusion and exclusion criteria, including moderate to severe throat pain intensity, as measured by a score≥7 on the Throat Soreness Scale (TSS), were admitted to the study.

Under double-blind conditions, each patient was randomly assigned one dose of ibuprofen 200 mg (ibuprofen); ibuprofen 200 mg with hydroxyzine 50 mg (ibuprofen/hydroxyzine); ibuprofen 200 mg with loratadine 20 mg (ibuprofen/loratadine); ibuprofen 200 mg with nizatidine 150 mg (ibuprofen/nizatidine); acetaminophen 500 mg (acetaminophen); acetaminophen 500 mg with ceterizine 20 mg (acetaminophen/ceterizine); celecoxib 200 mg (celecoxib); celecoxib 200 mg with ceterizine 20 mg (celecoxib/ceterizine); naproxen sodium 220 mg (naproxen); naproxen sodium 220 mg with loratadine 20 mg (naproxen/loratadine); or placebo. There were 9 patients randomly assigned to each treatment group.

Patients remained in the study center for a two-hour observed treatment period to assess their responses to study medication during the initial 2-hour post-dose period. They were discharged home for hourly assessments up to 6 hours post-dose. Patients were allowed alternative analgesic medication at any time during the study.

The Throat Soreness Scale (TSS), Swollen Throat Scale (SwoTS), Difficulty Swallowing Scale (DSS), Difficulty Talking Scale (DTS), and other Quality-of-Pain Scales were completed at Baseline (immediately pre-treatment). Each of these measurement instruments is a 0-10 ordinal scale (see TEST PROTOCOL below).

After administration of the assigned study medication, patients completed (1) the Throat Soreness Scale, (2) the Swollen Throat Scale, (3) the Difficulty Swallowing Scale, and (4) the Improvement Assessment (IA) every 15 minutes up to 2 hours. Measurements on the Difficulty Talking Scale and the Quality-of-Pain Scales were obtained after these four assessments at 60 minutes and at 2 hours after treatment.

After these $2^{nd}$ hour assessments, patients were discharged from the clinic with a Diary for entering responses on the Throat Soreness Scale, Swollen Throat Scale, Difficulty Swallowing Scale, Difficulty Talking Scale, and Improvement Assessment at 3, 4, 5, and 6 hours. After the 6 hour assessments, patients completed the Quality-of-Pain Scales.

Patients were seen at a Follow-Up Visit (usually the next day). At this visit they were shown each baseline rating scale and asked to indicate which level represented "definite improvement" to them (Definite Improvement Level), the Diary was reviewed for completeness by the Study Nurse, and ongoing evaluation and treatment were provided, if necessary, per standard clinic procedures.

After all coded patient data were verified by double entry, a statistician broke the randomization code and performed statistical analyses and tabulations.

Test Protocol

1. Study Procedures

Visit 1: Screening (Pre-Randomization Period)

Prior to study entry the following screening procedures will be performed:
  Informed Consent
  Medical History
  Physical Examination including Tonsillo-Pharyngitis Assessment, weight, height
  Vital Signs (oral temperature, pulse, respiratory rate), blood pressure
  Previous/Concomitant Medications Informed Consent Written informed consent must be obtained from each patient prior to the conduct of any study specific procedures. A copy of his/her signed consent form will be given to each patient.

Medical History

Each patient will provide a medical history including date of birth, duration and assessment of pharyngitis, including other symptoms of upper respiratory tract illness, significant past diseases/procedures and current conditions. All results will be recorded on the appropriate CRFs.

Physical Examination

Each patient will undergo a limited physical examination including height in inches, weight in pounds, evaluation of general appearance, ears, eyes, nose, and lungs, and the Tonsillo-Pharyngitis Assessment. All results will be recorded.

Vital Signs

Vital signs will be taken in the sitting position, including oral temperature, heart rate, respiratory rate and blood pressure. Screening vital signs should be taken within the 60 minutes prior to administration of the dose of study medication. This information will be recorded.

Laboratory Tests

There are no laboratory tests other than a Urine Pregnancy Test on eligible female patients. If the patient is a female of childbearing potential, a Urine Pregnancy Test will be performed, reviewed, and confirmed as negative prior to the patient's enrollment in the study. Results of the pregnancy test will be recorded on a Pregnancy Test Log and in the CRF.

Upon completion of the first 2 hours of the study or later, at the Investigator's medical discretion, laboratory tests for patients with pharyngitis (e.g., Abbott Quick 1-step Strep Test, throat culture, MonoSpot Test, CBC, etc.) may be performed according to standard medical procedures.

Previous/Concomitant Medications

The use of previous medications within the previous 7 days, including current (concomitant) medications, will be recorded at screening on the appropriate CRF.

Visit 1: Baseline

During the Baseline portion of the visit, the following procedures will be performed:
Patient Assessments
  Throat Soreness Scale
  Difficulty Swallowing Scale
  Swollen Throat Scale
  Difficulty Talking Scale
  Quality-of-Pain Scales (10)
Study Medication Administration
Patient Observation
Adverse Event Monitoring
Concomitant Medication
Patient Assessments At the Baseline portion of Visit 1, patients will be dispensed the patient assessment pages from the CRF (i.e., pages containing the rating scales for throat soreness, difficulty swallowing, swollen throat, difficulty talking, etc.) for use while in the unit and will be instructed on their use by the Study Nurse in order to capture all patient assessments directly from the patient.

The Study Nurse will review all data recorded by the patient. Data from the patient assessments will be transcribed onto the appropriate Summary Data CRF pages.

Study Medication Administration

The Medication Nurse will administer separately the two (2) study medication capsules assigned to the patient. Each patient will be observed to swallow each capsule with a few swallows of water, so that approximately 240 ml of water is consumed. The time of study medication administration and the patient's study medication number will be recorded in the source document and on the appropriate CRF.

"Nothing by mouth" except treatment will be allowed for two hours while at the site following study drug administration (e.g. no smoking, food, drink, candy, lozenges, etc.).

Patient Observation

Patients will remain in the research unit for observation during the two hour observed treatment period post administration of the dose of study medication.

Adverse Events

Details of adverse events occurring at Baseline and within 2 hours post administration of the first dose of study medication should be recorded in the source document and on appropriate CRFs.

Concomitant Medications

No other medications are permitted during the study (unless the patient requests rescue medication).

Visit 1: 15 Minutes Up to 2 Hours Post-Dose (Treatment Period)

During the period of 15 minutes up to 2 hours post administration of the dose of study medication (or just prior to receiving rescue medication), the following procedures will be performed at 15, 30, 45, 60, 75, 90, 105, and 120 minutes:
  Patient Observation
  Throat Soreness Scale
  Difficulty Swallowing Scale
  Swollen Throat Scale
  Improvement Assessment
  Rescue Medication
  Adverse Events Patient Observation Patients will remain in the research unit for observation during the two hour observed treatment period post administration of the dose of study medication.

Rescue Medication

The study site will supply one dose of rescue analgesic medication, acetaminophen 650 mg, for each patient.

The use of rescue analgesic medication should be delayed for at least two hours following consumption of the first dose of study medication, if possible. Rescue analgesic medication will be permitted at any time, as the needs of the patient dictate.

The following details concerning rescue analgesia will be collected: date and time taken, drug name and dose regimen. Just prior to taking rescue medication, patients will provide responses to pain assessments.

Patients taking rescue medication will be required to complete all efficacy assessments through 24 hours but these ratings will not be transcribed onto the CRFs and will not be analyzed.

Following dispensing or administration of rescue medication, acetaminophen 650 mg, the Investigator will provide advice for additional relief medication according to standard medical care. Any additional relief medication will be source documented and transcribed accordingly onto the concomitant medication CRF.

Adverse Events

Details of adverse events occurring up to 2 hours post administration of the study medication should be recorded in the source document and on the appropriate CRFs.

Visit 1:1 and 2 Hours Post-Dose (Treatment Period)

After the patient assessments at 1 hour and at 2 hours (or just prior to receiving rescue medication), the following procedures will also be performed:
  Difficulty Talking Scale
  Quality-of-Pain Scales (10)

Visit 1: 2 Hours Post-Dose or Withdrawal (Treatment Period)

At the end of the in-clinic treatment period (at 2 hours, i.e.), or just prior to receiving rescue medication or withdrawal due to reasons other than rescue medication, the following procedures will be performed:
  Vital Sign (oral temperature)
  Throat Soreness Scale
  Difficulty Swallowing Scale
  Swollen Throat Scale
  Improvement Assessment
  Difficulty Talking Scale
  Quality-of-Pain Scales (10)
  Rescue Medication
  Adverse Events
  Concomitant Medication(s)
  Collect Patient Assessment Pages
  Dispense Diary Vital Sign Oral temperature will be recorded on the appropriate CRF at the two-hour post-administration of study medication or within +/−5 minutes of receiving rescue medication or withdrawal due to reasons other than rescue medication.

Rescue Medication

The study site will supply one dose of rescue analgesic medication, acetaminophen 650 mg, for each patient.

The use of rescue analgesic medication should be delayed for at least two hours following consumption of the first dose of study medication, if possible. Rescue analgesic medication will be permitted at any time, as the needs of the patient dictate.

The following details concerning rescue analgesia will be collected: date and time taken, drug name and dose regimen. Just prior to taking rescue medication, patients will provide responses to pain assessments.

Patients taking rescue medication will be required to complete all efficacy assessments through 24 hours but these ratings will not be transcribed onto the CRFs and will not be analyzed.

Following dispensing or administration of rescue medication, acetaminophen 650 mg orally, the Investigator will provide advice about additional relief medication according to standard medical care. Any additional relief medication will be source documented and transcribed accordingly onto the concomitant medication CRF.

Adverse Events

Details of adverse events occurring at the end of the two hour observed treatment period or just prior to receiving rescue medication or withdrawal due to reasons other than rescue medication will be recorded in the source documents and on the appropriate CRFs.

Concomitant Medications

The use of concomitant medications during or at the end of the two-hour observed treatment period (if the patient has received rescue medication or if the patient has withdrawn due to reasons other than rescue medication) will be recorded on the appropriate CRFs.

Collect Patient Assessment Pages

The patient assessment pages of the CRF used during the patient's 2-hour evaluation in the unit will be collected and reviewed by the Study Nurse while the patient is still at the site. Data from the patient assessments will be transcribed onto the appropriate Summary Data CRF pages.

Dispense Diary

The patient will be discharged from the unit with a Diary. The Study Nurse will instruct the patient how to use the Diary on an hourly basis, filling out the following procedures at 3, 4, 5, and 6 hours:
  Throat Soreness Scale
  Swollen Throat Scale
  Difficulty Swallowing Scale
  Difficulty Talking Scale
  Improvement Assessment.

The Study Nurse will instruct the patient how to use the Diary by filling out the 10 Quality-of-Pain Scales after the other patient assessments are completed at 6 hours.

The patient will also be instructed to document any use of rescue medication and any adverse events that may occur The Study Nurse will also instruct the patient about study conditions through 6 hours:
  Alcohol and caffeine-containing beverages may not be consumed until after the 6-hour patient assessments.
  Patients who use inhaled steroids or β-agonists on an intermittent, as-needed basis and patients who use an antibiotic on a chronic basis (e.g., for acne) may use them after the 6-hour study period.
  Patients will be allowed food and drink between hours 2 and 6 only during the ½-hour after an hourly assessment.

In other words: Patients must take nothing by mouth during the ½-hour period prior to each hourly assessment.

Visit 2: Follow-Up Visit

The patient will return to the study site for the Follow-up Visit≤5 days post administration of study medication with his/her patient assessment diary. The following procedures will be performed:
  Definite Improvement Level
  Collect Diary
  Adverse Events
  Concomitant Medications Definite Improvement Level Patients will be dispensed the patient assessment pages from the CRF (i.e., pages containing the Baseline rating scales for throat soreness, difficulty swallowing, swollen throat, difficulty talking, etc.) and will be instructed on their use by the Study Nurse in order to capture all patient assessments directly from the patient.

The Study Nurse will review all data recorded by the patient. Data from the patient assessments will be transcribed onto the appropriate Summary Data CRF page.

Collect Diary

The patient assessment diary will be collected at the Final Visit. The Study Nurse will review the patient assessment diary while the patient is still at the site. Data from the patient assessments will be transcribed onto the appropriate Summary Data CRF pages.

Adverse Events

The patient assessment diary will be collected and reviewed and the patient will be queried about all adverse events experienced during the period between discharge from the unit and the Follow-up Visit. All adverse events will be recorded in the source documents and on the appropriate CRFs.

Concomitant Medications

The patient will be queried about all medication taken during the period between discharge from the unit and the Follow-up Visit. Information about any concomitant medications will be transcribed onto the appropriate CRFs.

Patient Withdrawal

A completed patient is one who completes all of the 2-hour patient assessments. If for any reason a patient is withdrawn before completing the study or before Visit 2, the reason for withdrawal must be entered on the End of Study Form and all appropriate CRFs must be completed. All final assessments should be performed as described for Visit 2 (Follow-up Visit). Patients who terminate study participation before Visit 2 due to an adverse event will be reported as withdrawing due to an "adverse event."

2. Assessments

Tonsillo-Pharyngitis Assessment (TPA)

The Study Nurse will rate each patient for objective findings that confirm the diagnosis of tonsillo-pharyngitis at screening. The seven variables below will be rated on semi-quantitative scales with values of 0, 1, 2, 3. The values will be added together to make a Tonsillo-Pharyngitis Assessment (TPA) that can range from 0 to 21 points. The patient must have a minimum of 5 points on the 21-point TPA of the physical examination to qualify for study inclusion:

|  | 0 Points | 1 Point | 2 Points | 3 Points |
| --- | --- | --- | --- | --- |
| Oral Temperature | ≤98.6° F. | 98.7-98.9° F. | 99.0-99.9° F. | ≥100.0° F. |
| Oropharyngeal color | Normal/Pink | Slightly Red | Red | Beefy red |
| Size of Tonsils | Normal/absent | Slightly enlarged | Moderately enlarged | Much enlarged |
| Number of oropharyngeal exanthems (vesicles, petechiae, or exudates) | None | Few | Several | Many |
| Largest size of anterior cervical lymph nodes | Normal | Slightly enlarged | Moderately enlarged | Much enlarged |
| Number of anterior cervical lymph nodes | Normal | Slightly increased | Moderately increased | Greatly Increased |
| Maximum tenderness of some anterior cervical lymph nodes | Not tender | Slightly tender | Moderately tender | Very tender |

Results of the Tonsillo-Pharyngitis Assessment will be recorded on the appropriate CRF.

Throat Soreness Scale (TSS)

The patient will be asked to evaluate his/her throat soreness using a 0-to-10 ordinal scale at Baseline as well as at 15, 30, 45, 60, 75, 90, 105 and 120 min and then hourly through 6 hours. The patient will be requested to swallow and instructed:

"Circle the number that shows how sore your throat is now when you swallow:"

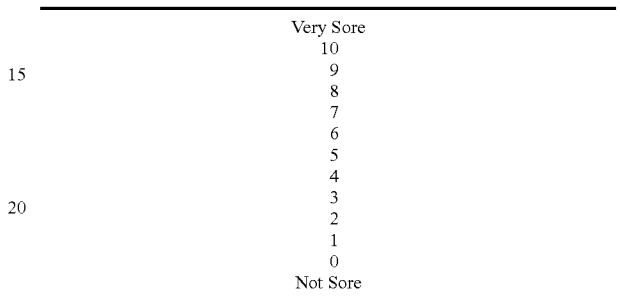

Data from this scale will be transcribed onto the appropriate Summary Data CRFs.

Difficulty Swallowing Scale, Swollen Throat Scale, Difficulty Talking Scale

The patient will be asked to evaluate his/her difficulty swallowing (dysphagia), how swollen the throat feels, and his/her difficulty speaking using separate 0-to-10 ordinal scales at Baseline and at 15, 30, 45, 60, 75, 90, 105, and 120 minutes and at 3, 4, 5, and 6 hours post dose. The patient will be instructed to swallow and instructed:

"Circle the number that best describes how your throat feels now."

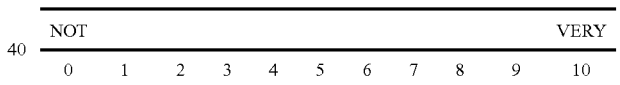

Data from these scales will be transcribed onto the appropriate Summary Data CRFs.

Quality-of-Pain Scales for the Throat

The patient will be asked to evaluate 7 other sensory qualities of pain (hot, scratchy, raw, raspy, tight, dry, burning), 2 affective qualities of pain (irritating, annoying), and another evaluative quality of pain (it hurts) using separate 0-to-10 ordinal scales at Baseline and at 1 hour, 2 hours, and 6 hours post dose. The patient will be instructed to swallow and instructed:

"For each word, circle the number that best describes how your throat feels now."

Data from these scales will be transcribed onto the appropriate Summary Data CRFs.

Improvement Assessment

The patient will grade the improvement of his/her throat at 15, 30, 45, 60, 75, 90, 105, and 120 minutes, and at 3, 4, 5, and 6 hours post dose using a 5-category transitional scale. The patient will be instructed:

"Considering how your throat felt before you took the study medicine, circle the response that best describes how your throat is now."

Grading
no improvement
some improvement
50% improvement
definite improvement
100% improvement Data from this scale will be transcribed onto the appropriate Summary Data CRFs.

Definite Improvement Level (DIL)

After the patient is shown his/her completed Baseline Throat Soreness Scale, the Study Nurse will point to the number which the patient marked at Baseline and instruct the patient:

"Starting at this level with your sore throat, at and below which number means definite improvement to you?"

Next, the Study Nurse will separately show the patient his/her Baseline Difficulty Swallowing Scale, Swollen Throat Scale, Difficulty Talking Scale, and each of the 10 Quality-of-Pain Scales, with the same instructions for each scale.

Data from the Definite Improvement Level for each scale will be transcribed on the appropriate Summary Data CRF.

3. Adverse Event

Definition of an Adverse Event

An adverse event is any untoward medical occurrence in a clinical investigation patient administered a product or medical device; the event need not necessarily have a causal relationship with the treatment or usage. Examples of adverse events include but are not limited to:

Abnormal test findings;
Clinically significant symptoms and signs;
Changes in physical examination findings;
Hypersensitivity;
Progression/worsening of underlying disease.

Additionally, they may include the signs or symptoms resulting from:

Drug overdose;
Drug withdrawal;
Drug abuse;
Drug misuse;
Drug interactions;
Drug dependency;
Extravasation;
Exposure in utero.

Abnormal Test Findings

The criteria for determining whether an abnormal objective test finding should be reported as an adverse event are as follows:

Test result is associated with accompanying symptoms, and/or
Test result requires additional diagnostic testing or medical/surgical intervention, and/or
Test result leads to a change in study dosing or discontinuation from the study, significant additional concomitant drug treatment, or other therapy, and/or
Test result is considered to be an adverse event by the Investigator or sponsor.

Merely repeating an abnormal test, in the absence of any of the above conditions, does not constitute an adverse event. Any abnormal test result that is determined to be an error does not require reporting as an adverse event.

Serious Adverse Events

A serious adverse event or serious adverse drug reaction is any untoward medical occurrence at any dose that:

Results in death;
Is life-threatening (immediate risk of death);
Requires inpatient hospitalization;
Results in persistent or significant disability/incapacity;
Results in congenital anomaly/birth defect.

4. Data Display and Analysis/Statistical Methods 4.1. Populations of Analysis

Safety Population:

A patient will be included in the Safety Population if the patient was randomized and swallowed the full dose of study medication. The Safety Population will be used for the safety analysis. Patients in this population will be assigned to the treatment group corresponding to the treatment they received during the study.

Efficacy Population:

Patients who are randomized to treatment, have received the full dose of study medication and have completed all post-treatment assessments for a particular efficacy variable will form the efficacy population for that variable. The efficacy population will be used for analysis of primary and secondary endpoints.

Demographics and Baseline Characteristics:

Demographic and Baseline characteristics will be summarized using descriptive statistics, including the number of patients in each treatment group, mean, standard deviation, median and range for continuous variables; frequency and percent for categorical variables; etc.

Sample Size Determination

The sample size (9 patients per treatment group) is considered sufficient for proof-of-concept research. Statistical analyses will be performed when feasible, but it is not anticipated that there will be sizable treatment differences for statistical comparisons between treatment groups.

4.3. Randomization

Patients who qualify will be assigned at the site in the order in which they are enrolled in the study. They will receive their allocated treatment according to a computer-generated randomization schedule prepared prior to the start of the study.

Efficacy Analysis

Efficacy data that can be analyzed will be analyzed using the Efficacy Population. All comparisons will be one-sided at an alpha level of 0.05 and all point estimates will be accompanied by 95% confidence intervals.

Analysis/Display of Primary Endpoints

Primary Endpoint Variable:

Difference in throat soreness over 6 hours

The primary endpoint variable is the Summed Difference in Throat Soreness at 6 hours, which is based on the Throat Soreness Scale. The patient will be asked to evaluate his/her throat soreness, using a 0-to-10 ordinal scale at baseline and at 15, 30, 45, 60, 75, 90, 105 minutes and 2, 3, 4, 5, and 6 hours. At each time point post-dose, a difference is calculated between the throat soreness at that time and the patient's baseline throat soreness. The time-weighted Summed Difference in Throat Soreness at each time point is calculated as the sum of the differences from baseline until that time point.

The Summed Difference in Throat Soreness at 6 hours will be displayed and analyzed by comparing treatment groups (e.g., ibuprofen 200 mg with hydroxyzine 50 mg to ibuprofen 200 mg) using a general linear model with treatment and baseline Throat Soreness as fixed effects. The difference and 95% confidence interval for the difference of treatment effects will be calculated using least squares means. Alternate methods of display and analysis may be used when appropriate (including sub-analyses based on cogent clinical features such as relatively high baseline throat soreness, difficulty swallowing, swollen throat).

Analysis/Display of Secondary Endpoints

Secondary Endpoint Variables:
a. Difference in Quality-of-Pain Index* over 6 hours
b. Difference in Throat Function Index** over 6 hours
c. Difference in difficulty swallowing over 6 hours
d. Difference in throat swelling over 6 hours
e. Difference in relatively severe (baseline>7) qualities of pain over 6 hours
f. Difference in relatively severe sensory qualities of pain over 6 hours
g. Difference in the most severe quality(ies) of pain*** over 6 hours
h. Difference in relatively severe difficulty swallowing at 6 hours
i. Difference in relatively severe difficulty talking at 6 hours
j. Differences in difficulty swallowing at individual time points
k. Differences in throat soreness at individual time points
l. Differences in throat swelling at individual time points
m. Percentage of patients with definite improvement over 6 hours
n. Total improvement over 6 hours
o. Improvement at individual time points For each treatment group, results for improvement and differences from baseline will be reported and displayed for individual patients and as medians, percentage differences, etc. Alternate methods of display and analysis will be examined, including sub-analyses based on cogent clinical features (such as relatively high baseline difficulty swallowing, throat soreness, swollen throat) and based on the pharmacologic time-effect curves of the drugs being tested (i.e., onset time within the first 2 hours after drug administration).

*Throat soreness (an evaluative quality of pain), throat swelling (a sensory quality of pain), and the other 10 qualities of throat pain comprise the 120-point Quality-of-Pain Index.
**Difficulty Swallowing and Difficulty Talking comprise the 20-point Throat Function Index.
***The most severe quality of pain has the highest baseline score. Qualities that have the same highest baseline score (ties) may also be examined. The "most severe qualities" will be analyzed separately and as a group since these kinds of discomfort represent the most bothersome from the patient's point of view - - - in keeping with the guiding principle and focus of this research, "patient-oriented" clinical effects.

4.4.3. Comparisons of Interest
1. Ibuprofen 200 mg+hydroxyzine 50 mg vs. ibuprofen 200 mg (analgesic potentiation by hydroxyzin)
2. Ibuprofen 200 mg+loratadine 20 mg vs. ibuprofen 200 mg (analgesic potentiation by loratadine)
3. Acetaminophen 500 mg+ceterizine 20 mg vs. acetaminophen 500 mg (analgesic potentiation by ceterizine)
4. Celecoxib 200 mg+ceterizine 20 mg vs. celecoxib 200 mg (analgesic potentiation by ceterizine)
5. Naproxen sodium 220 mg+loratadine 20 mg vs. naproxen sodium 220 mg (analgesic potentiation by loratadine)
6. Ibuprofen 200 mg+nizatadine 150 mg vs. ibuprofen 200 mg (analgesic potentiation by nizatidine)
7. Ibuprofen 200 mg vs. placebo (efficacy of ibuprofen 200 mg, assay sensitivity, validation of rating scales)
8. Naproxen sodium 220 mg vs. placebo (efficacy of naproxen sodium 220 mg, assay sensitivity, validation of rating scales)
9. Acetaminophen 500 mg vs. placebo (efficacy of acetaminophen 500 mg, assay sensitivity, validation of rating scales)
10. Celecoxib 200 mg vs. placebo (efficacy of celecoxib 200 mg, assay sensitivity, validation of rating scales)
11. Each combination vs. placebo at individual time points (onset of action, peak effect, duration of action)
12. Same antihistamine when combined with different analgesics (differential effects of same dose of antihistamine with different analgesics)
13. Comparisons of single-ingredient analgesics (relative onset, peak, duration and overall analgesia)
14. Comparisons of the pooled combination treatment arms to each single analgesic.

4.4.4. Other Endpoints

Sensitivity appraisals and internal validation of measurements on the 12 quality-of-pain rating scales, the 2 throat function scales, and the improvement assessment by examining the comparison of ibuprofen 200 mg, the positive control, with placebo (and confirming assay sensitivity by examining the comparisons of each active drug - - - naproxen sodium 220 mg, acetaminophen 500 mg, celecoxib 200 mg - - - with placebo).

External validation of measurements on the quality-of-pain rating scales, the throat function scales, and the improvement assessment by examining the comparison of ibuprofen 200 mg with placebo on these scales and correlating these measurements with those from the throat soreness scale, a validated scale (the "Lasagna Pain Scale"). Confirmatory assessments will also be conducted by examining the comparisons of each other active drug - - - naproxen sodium 220 mg, acetaminophen 500 mg, celecoxib 200 mg - - - with placebo and correlating these measurements with those from the throat soreness scale.

Results of Study

A total of 99 patients were enrolled in the study. Nine patients were randomly assigned to each of the 11 treatment groups. All patients had physical evidence of tonsillopharyngitis and moderately severe sore throat at baseline (median TSS=7). Baseline demographic and clinical characteristics were similar across all treatment groups.

Among the 99 patients studied, 8 (8%) had documented infection with Group A, beta-hemolytic Streptococcus ("Strep throat") and 4 (4%) had documented infectious mono-nucleosis ("Mono") and received appropriate antibiotic treatment at study conclusion.

Analyses were performed on all 99 patients ("intent-to-treat analyses"). There were 14 patients who used additional analgesic treatment during the 6-hour observation period; for each subsequent evaluation for these patients, the "last observation (was) carried forward." Statistical comparisons (between each active drug and placebo, between each antihistamine/analgesic and placebo, between each antihistamine/analgesic and the corresponding single analgesic) were performed using the Wilcoxon Rank Sum Test. Definite Improvement Level comparisons were performed using Fisher's Exact Test. Correlations between each new rating scale and the TSS were performed using Spearman Rank Correlation.

Efficacy Variables

To identify the efficacy of each antihistamine/analgesic combination compared to a single-ingredient analgesic and to validate and determine the sensitivity of each new measurement instrument, results over the 6-hour observation period are presented separately for the standard measurement instrument, the Throat Soreness Scale, and for each new method.

A. Throat Soreness Scale (TSS)

As seen in FIG. 1, all "positive control drugs" (i.e., the standard drugs ibuprofen, acetaminophen, celecoxib, naproxen) were differentiated from placebo. Acetaminophen and celecoxib demonstrated significantly greater reduction in throat soreness compared to placebo over 6 hours (both $p<0.05$), with a trend ($p=0.10$) for ibuprofen compared to placebo. All antihistamine/analgesic combinations also differed from placebo.

Figure 2:
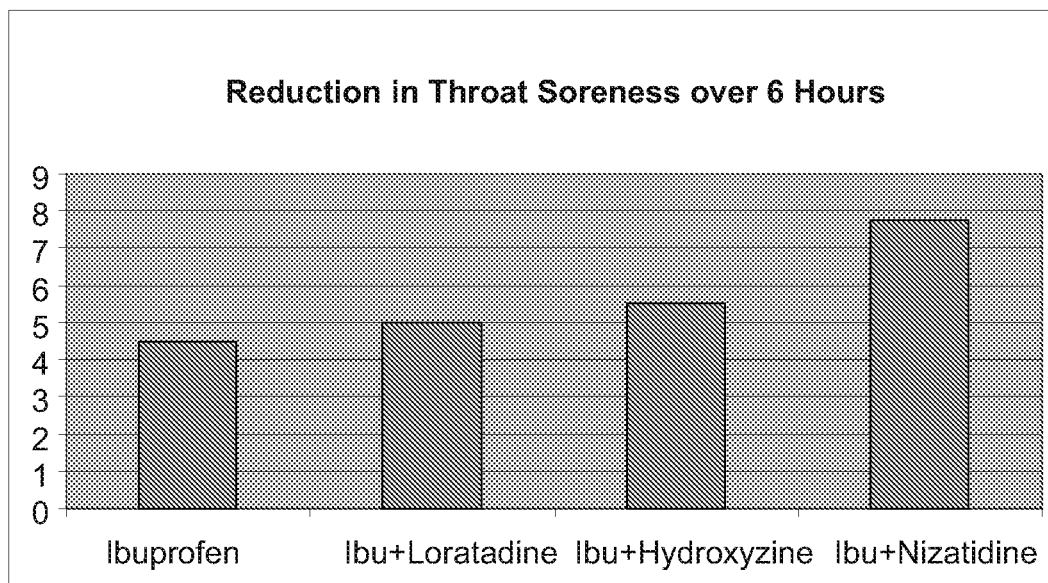
FIG. 2 shows the reduction in throat soreness over 6 hours of ibuprofen 200 mg (Ibu) and several ibuprofen combinations (ibuprofen 200 mg+loratadine 20 mg (Ibu+Loratadine), ibuprofen 200 mg+hydroxyzine 50 mg (Ibu+Hydroxyzine), ibuprofen 200 mg+nizatidine 150 mg (Ibu+Nizatidine).

As seen in FIG. 2, the comparison of ibuprofen/loratadine to ibuprofen revealed an 11% difference in the median total reduction of TSS over 6 hours. The comparison of ibuprofen/hydroxyzine to ibuprofen revealed a 22% difference in TSS reduction over 6 hours. The comparison of ibuprofen/nizatidine to ibuprofen revealed a 73% difference in TSS reduction over 6 hours ($p=0.05$).

There was no evidence of enhanced overall analgesic effect on the TSS for the comparison of acetaminophen/ceterizine to acetaminophen alone, for the comparison of celecoxib/ceterizine to celecoxib alone, or for the comparison of naproxen/loratadine to naproxen alone.

Figure 3:
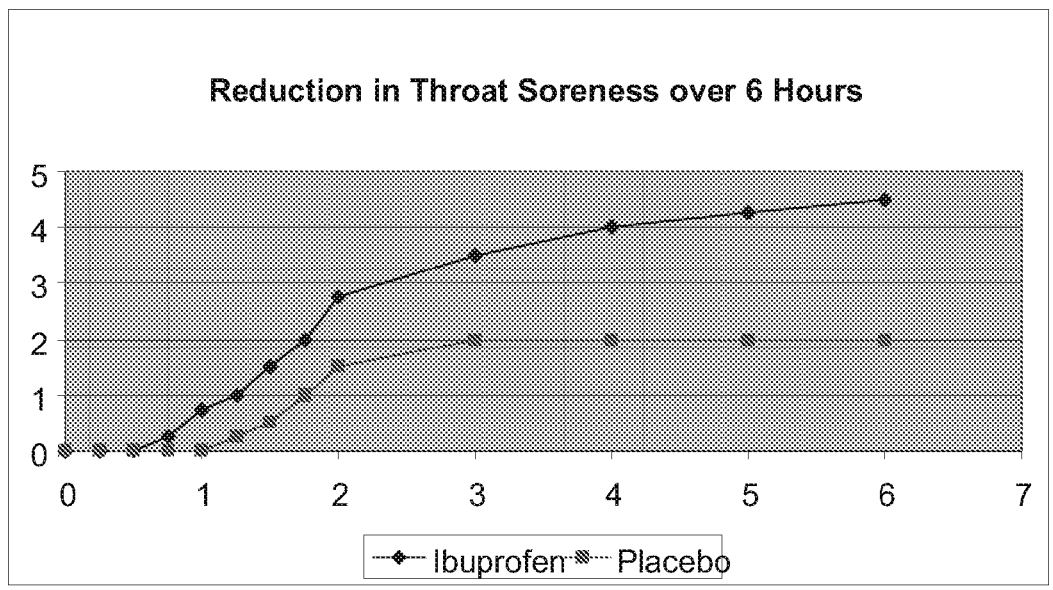
FIG. 3 shows the reduction in throat soreness at time points over 6 hours of ibuprofen 200 mg and placebo.

All active single- and combination-ingredient drugs also demonstrated greater analgesic efficacy compared with placebo in terms of throat soreness difference at individual time points, showing pharmacodynamic curves typical of analgesic drugs. Acetaminophen separated from placebo from 15 minutes through 6 hours; ibuprofen separated from placebo from 30 minutes through 6 hours (FIG. 3), as did naproxen and celecoxib. There were no apparent differences between any of the single-ingredient analgesics.

TSS scores showed differences from placebo for ibuprofen/loratadine beginning at 15 minutes; for ibuprofen/nizatidine and for celecoxib/ceterizine beginning at 30 minutes; and for ibuprofen/hydroxyzine beginning at 45 minutes.

In summary, evidence of analgesic potentiation was detected on the TSS in three comparisons:
1. ibuprofen/hydroxyzine vs. ibuprofen, identifying analgesic potentiation by hydroxyzine;
2. ibuprofen/loratadine vs. ibuprofen, identifying analgesic potentiation by loratadine when combined with ibuprofen; and
3. ibuprofen/nizatidine vs. ibuprofen, identifying analgesic potentiation by nizatidine.

The most pronounced effects were noted when ibuprofen was combined with the $H_2$-antagonist, nizatidine, greater than ibuprofen alone (perhaps because of the faster bioavailability of nizatidine powder delivered from a capsule, compared to the bioavailability of ibuprofen delivered from a coated compressed tablet).

Ceterizine showed some enhancement of the onset of analgesic action by celecoxib, suggesting that an adequately sized onset-of-action study might discern this contribution to pharmacodynamic activity. Overall, however, there was no evidence on the TSS of analgesic potentiation by ceterizine when combined with acetaminophen or celecoxib. And, while loratadine does augment ibuprofen's analgesia as measured on the TSS, at this stage in our research it appears that loratadine provides no detectable analgesic potentiation when combined with naproxen sodium (suggesting that the naproxen sodium salt, unlike ibuprofen, may interfere with loratadine activity).

B. Improvement Assessment (IA)

Measurements on the Improvement Assessment (IA) revealed differences between the active control drugs (ibuprofen, acetaminophen, celecoxib, naproxen) and placebo over 6 hours as well as between each antihistamine/analgesic and placebo.

In fact, 9/9 patients who received acetaminophen or ibuprofen achieved at least some improvement within 1 hour, as did 7/9 patients who received celecoxib or naproxen, compared with 4/9 patients who received placebo. Similarly, 9/9 patients who received ibuprofen/nizatidine, 8/9 patients who received acetaminophen/ceterizine or ibuprofen/hydroxyzine, 7/9 patients who received ibuprofen/loratadine, and 6/9 patients who received naproxen/loratadine achieved at least some improvement within 1 hour.

In terms of onset of action, 8/9 patients who received acetaminophen achieved at least some improvement within 30 minutes, as did 6/9 patients who received ibuprofen, 4/9 patients who received naproxen, and 3/9 patients who received celecoxib, compared with 1/9 of patients who received placebo.

There was similar direct evidence of onset by the antihistamine/analgesic combinations detected on the IA: 6/9 patients who received ibuprofen/nizatidine, 5/9 patients who received acetaminophen/ceterizine, 4/9 patients who received ibuprofen/loratadine or celecoxib/ceterizine, and 3/9 patients who received ibuprofen/hydroxyzine or naproxen/loratadine achieved at least some improvement over the first 30 minutes, compared with 1/9 of patients who received placebo.

Although no differences between combination and single-ingredient analgesics were detected, this method of examining the IA over the initial 30 minutes after drug administration was very sensitive to the identification of onset of drug action.

Over the 6-hour treatment period, 7/9 patients who received acetaminophen and 8/9 patients who received celecoxib achieved at least 50% improvement, as did 4/9 patients who received ibuprofen or naproxen, compared with 2/9 patients who received placebo.

Similarly, 8/9 patients who received ibuprofen/nizatidine, 7/9 patients who received ibuprofen/hydroxyzine, 5/9 patients who received ibuprofen/loratadine or celecoxib/ceterizine, and 4/9 patients who received naproxen/loratadine achieved at least 50% improvement over 6 hours, compared with 2/9 patients who received placebo.

Analyses of total improvement over 6 hours identified 27% difference between ibuprofen/loratadine and ibuprofen, 18% difference between ibuprofen/hydroxyzine and ibuprofen, and 36% difference between ibuprofen/nizatidine and ibuprofen.

There was no evidence of enhanced overall analgesic effect on the IA for comparisons of acetaminophen/ceterizine to acetaminophen alone, of celecoxib/ceterizine to celecoxib alone, or of naproxen/loratadine to naproxen alone.

All active single- and combination-ingredient drugs also demonstrated greater improvement than placebo at individual time points, showing pharmacodynamic curves typical of analgesic drugs. The IA curves for acetaminophen and ibuprofen separated from placebo from 30 minutes through 6 hours; celecoxib and naproxen from 45 minutes through 6 hours. There were no apparent differences between any of the single-ingredient analgesics.

IA scores showed differences from placebo for acetaminophen/ceterizine and ibuprofen/nizatidine beginning at 30 minutes; for ibuprofen/loratadine, ibuprofen/hydroxyzine, and celecoxib/ceterizine beginning at 45 minutes; and for naproxen/loratadine beginning at 60 minutes.

In sum, evidence of analgesic potentiation was detected on the IA in the comparisons of ibuprofen/loratadine vs. ibuprofen, of ibuprofen/hydroxyzine vs. ibuprofen, and, in particular, of ibuprofen/nizatidine vs. ibuprofen.

C. Definite Improvement Level (DIL)

According to the criterion of achieving the Definite Improvement Level particular for each rating scale, use of the DIL revealed differences between the active control drugs (ibuprofen, acetaminophen, celecoxib, naproxen) and placebo.

Figure 4:
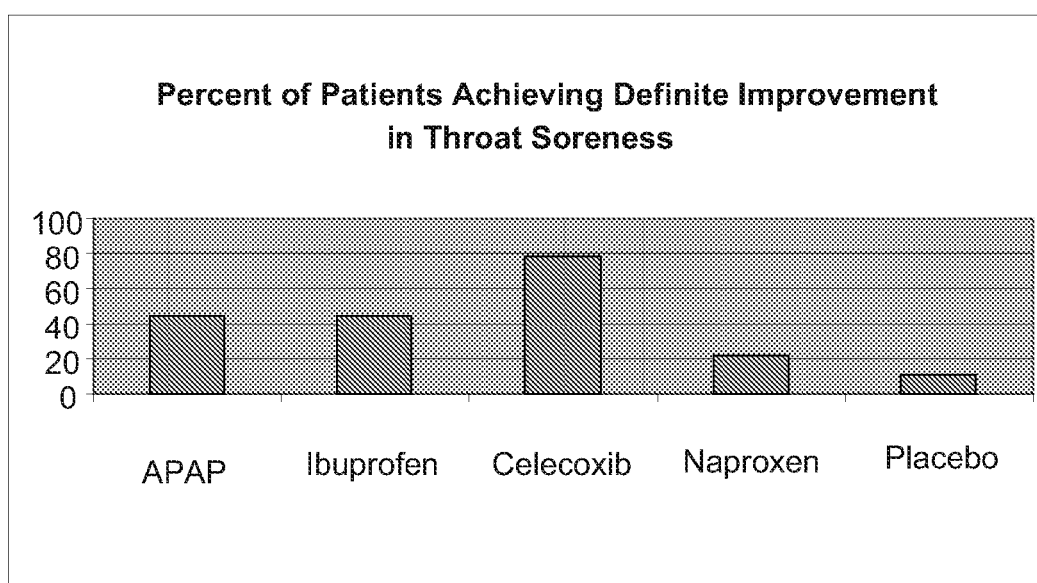
FIG. 4 shows the percentage of patients who achieved their own Definite Improvement Level on the Throat Soreness Scale of several analgesics and placebo.

As shown in a representative use of the DIL, for TSS scores (FIG. 4), 11.1% (1/9) of patients who received placebo achieved their own Definite Improvement Level on the TSS, compared to 44.4% of the patients who received acetaminophen or ibuprofen, 77.7% of patients who received celecoxib ($p<0.01$), 22.2% of patients who received naproxen.

Similar differentiation of active drugs from placebo was detected on the DIL for other rating scales. For example:

(1) 11.1% (1/9) of patients who received placebo achieved their own Definite Improvement Level on the Difficulty Swallowing Scale, compared to 55.6% of patients who received acetaminophen, 44.4% of patients who received ibuprofen, 66.7% of patients who received celecoxib ($p=0.05$), 33.3% of patients who received naproxen;

(2) 22.2% (2/9) of patients who received placebo achieved their own Definite Improvement Level on the Swollen Throat Scale, compared to 66.7% of patients who received acetaminophen, 44.4% of patients who received ibuprofen, 77.8% of the patients who received celecoxib ($p=0.06$), 44.4% of patients who received naproxen;

(3) 11.1% (1/9) of patients who received placebo achieved their own Definite Improvement Level on the "It hurts" Quality-of-Pain Scale, compared to 55.6% of patients who received acetaminophen or celecoxib, 33.3% of patients who received ibuprofen or naproxen;

(4) 22.2% (2/9) of patients who received placebo achieved their own Definite Improvement Level on the "Annoying" Quality-of-Pain Scale, compared to 66.7% of patients who received acetaminophen, 33.3% of the patients who received ibuprofen or naproxen, 55.6% of the patients who received celecoxib.

With distinct differentiations of active drugs and antihistamine/analgesic combinations from placebo, the Definite Improvement Level system was thus validated as a measurement instrument. Using the DIL measure, differences were clearly seen between antihistamine/analgesic combinations and placebo on different rating scales. However, the DIL did not differentiate antihistamine/analgesic combinations from single analgesics perhaps because, as a nominal scale (i.e., definite improvement, no definite improvement), the DIL identifies the presence (or absence) of drug activity, not differences between degrees of response.

D. Difficulty Swallowing Scale (DSS)

Acetaminophen, ibuprofen, and celecoxib demonstrated greater reduction in difficulty swallowing compared with placebo over 6 hours. There was a significant difference between acetaminophen and placebo on the DSS ($p=0.01$). This differentiation of known active analgesic drugs from placebo serves as a source of internal validation of the DSS. Indeed, ratings on the DSS correlated with ratings on the TSS ($r=0.80$, $p<0.0001$).

Ibuprofen/loratadine, ibuprofen/hydroxyzine, ibuprofen/nizatidine, and celecoxib/ceterizine also differed from placebo on this measurement.

Figure 5:
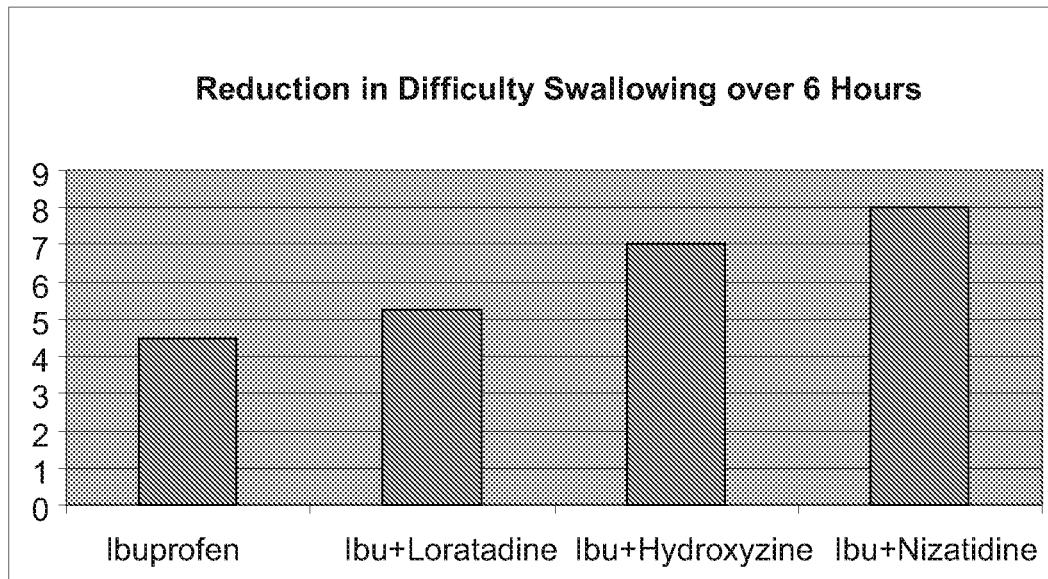
FIG. 5 shows the reduction in difficulty swallowing over 6 hours of ibuprofen combinations and ibuprofen 200 mg.

As seen in FIG. 5, the comparison of ibuprofen/loratadine to ibuprofen revealed an 18% difference in the total reduction of DSS over 6 hours. The comparison of ibuprofen/hydroxyzine to ibuprofen revealed a 55% difference in DSS reduction over 6 hours. The comparison of ibuprofen/nizatidine to ibuprofen revealed a 78% difference in DSS reduction over 6 hours.

There was no evidence of enhanced overall analgesic effect on the DSS for the comparisons of acetaminophen/ceterizine to acetaminophen, of celecoxib/ceterizine to celecoxib, or of naproxen/loratadine to naproxen.

All single- and combination-ingredient drugs also demonstrated greater analgesic efficacy compared with placebo in terms of a difference in difficulty swallowing at individual time points, showing pharmacodynamic curves typical of analgesic drugs.

It should be noted that, because patients were admitted to the study regardless of the severity of their pre-treatment difficulty swallowing, which ranged from 0 to 10 (i.e., all patients' baseline DSS scores were not $\geq 7$, as required for the TSS), these findings represent underestimates of treatment effects detected on the Difficulty Swallowing Scale.

In sum, evidence of analgesic potentiation was detected on the functional DSS in three comparisons:

1. ibuprofen/hydroxyzine vs. ibuprofen, identifying analgesic potentiation by hydroxyzine;
2. ibuprofen/loratadine vs. ibuprofen, identifying analgesic potentiation by loratadine when combined with ibuprofen; and
3. ibuprofen/nizatidine vs. ibuprofen, identifying analgesic potentiation by nizatidine.

The most pronounced effects were noted when ibuprofen was combined with nizatidine, greater than ibuprofen alone. There was no evidence of analgesic potentiation by ceterizine when combined with acetaminophen or celecoxib. Finally, while loratadine does augment ibuprofen's analgesia as measured on the DSS, it appears that loratadine provides no detectable analgesic potentiation when combined with naproxen sodium (perhaps because the naproxen sodium salt interferes with loratadine activity).

E. Difficulty Talking Scale (DTS)

Figure 6:
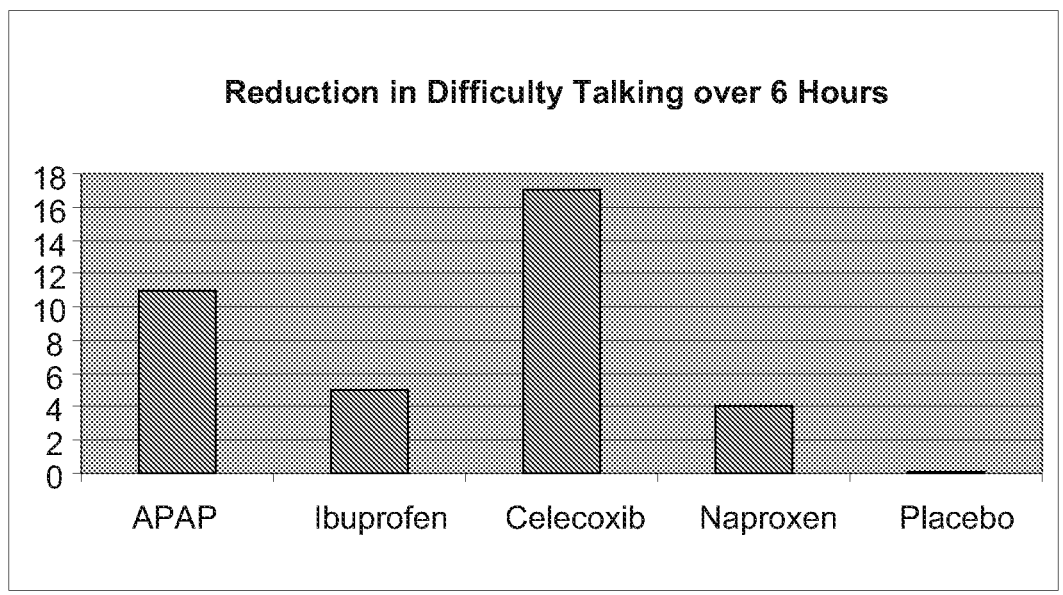
FIG. 6 shows the reduction in difficulty talking over 6 hours of several analgesics and placebo.

All four positive control drugs demonstrated greater reduction in difficulty talking compared with placebo over 6 hours (FIG. 6). The differences between acetaminophen compared to placebo and between celecoxib compared to placebo were significant on the DTS (both $p<0.05$). This differentiation of known active analgesic drugs from placebo serves as a source of internal validation of the DTS, which correlated with ratings on the TSS ($r=0.54$, $p<0.0001$).

All antihistamine/analgesic combinations also differed from placebo on the DTS.

Figure 7:
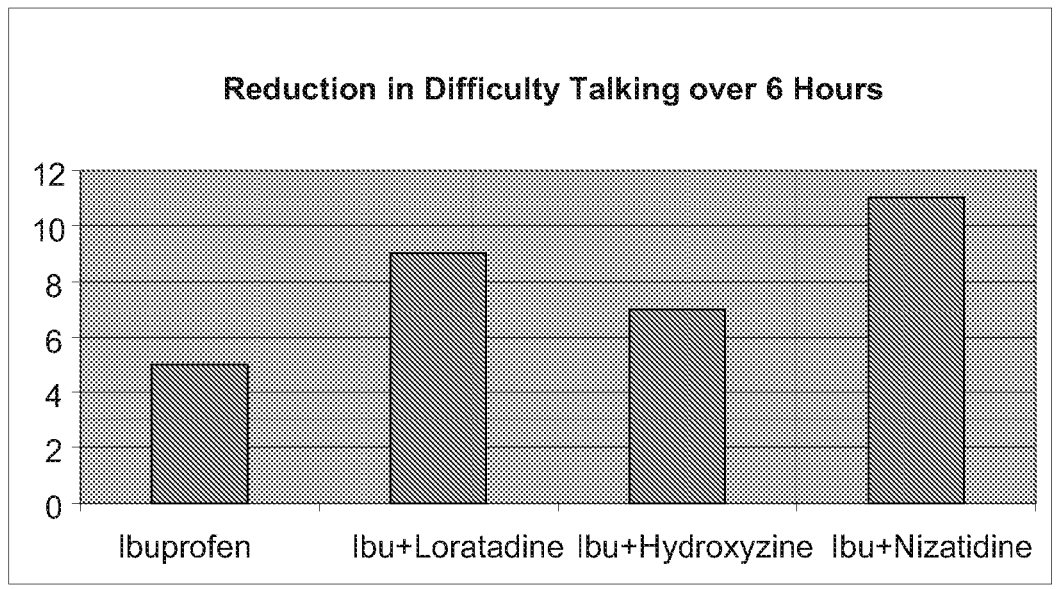
FIG. 7 shows the reduction in difficulty talking over 6 hours of ibuprofen combinations and ibuprofen 200 mg.

The comparison of ibuprofen/loratadine to ibuprofen revealed 80% difference in the total reduction of DTS over 6 hours (FIG. 7). The comparison of ibuprofen/hydroxyzine to ibuprofen revealed 40% difference in DTS reduction over 6 hours. The comparison of ibuprofen/nizatidine to ibuprofen revealed 120% difference in DTS reduction over 6 hours.

There was no evidence of enhanced overall analgesic effect on the DTS for the comparison of acetaminophen/ceterizine to acetaminophen, the comparison of celecoxib/ceterizine to celecoxib, or the comparison of naproxen/loratadine to naproxen.

All single- and combination-ingredient drugs also demonstrated greater analgesic efficacy compared with placebo in terms of a difference in difficulty talking at individual time points, showing pharmacodynamic curves typical of analgesic drugs.

Because patients were admitted to the study regardless of the severity of their pre-treatment DTS (which ranged from 0 to 10, i.e., not $\geq 7$, as required for the TSS), these findings represent underestimates of treatment effects measured on the DTS. Nevertheless, the extremely low placebo response when patients used the DTS is noteworthy.

In sum, evidence of analgesic potentiation was detected on the functional DTS in four comparisons:
1. ibuprofen/hydroxyzine vs. ibuprofen, identifying analgesic potentiation by hydroxyzine;
2. ibuprofen/loratadine vs. ibuprofen, identifying analgesic potentiation by loratadine when combined with ibuprofen; and
3. ibuprofen/nizatidine vs. ibuprofen, identifying analgesic potentiation by nizatidine.

There was no evidence of analgesic potentiation by ceterizine when combined with acetaminophen or celecoxib. As on other scales, while loratadine does augment ibuprofen's analgesia as measured on the DTS, it appears that loratadine provides no detectable analgesic potentiation when combined with naproxen sodium.

F. Throat Function Index (TFI)

Acetaminophen and celecoxib demonstrated significantly greater reduction in the TFI (a summary index of the two throat functions, swallowing and talking) compared with placebo over 6 hours (both $p \leq 0.01$). This clear differentiation of known active analgesic drugs from placebo serves as a source of internal validation of the TFI. Ratings on the TFI correlated with ratings on the TSS ($r=0.76$, $p<0.0001$).

With the exception of the comparison of acetaminophen/ceterizine to placebo, all antihistamine/analgesic combinations differed from placebo on the TFI, too.

The comparison of ibuprofen/loratadine to ibuprofen and of ibuprofen/hydroxyzine to ibuprofen revealed 100% differences in the total reduction of TFI over 6 hours. The comparison of ibuprofen/nizatidine to ibuprofen revealed 142% difference in TFI reduction over 6 hours. There was no evidence of enhanced overall analgesic effect on the TFI for the comparisons of acetaminophen/ceterizine or celecoxib/ceterizine to the single analgesic or the comparison of naproxen/loratadine to naproxen.

All single- and combination-ingredient drugs also demonstrated greater analgesic efficacy compared with placebo in terms of a difference in throat function at individual time points, showing pharmacodynamic curves typical of analgesic drugs.

However, because patients were admitted to the study regardless of the severity of their pre-treatment TFI (which ranged from 4 to 20), these findings represent underestimates of treatment effects measured on the TFI.

In sum, evidence of analgesic potentiation was detected on the TFI in three comparisons:
1. ibuprofen/hydroxyzine vs. ibuprofen, identifying analgesic potentiation by hydroxyzine;
2. ibuprofen/loratadine vs. ibuprofen, identifying analgesic potentiation by loratadine when combined with ibuprofen; and
3. ibuprofen/nizatidine vs. ibuprofen, identifying analgesic potentiation by nizatidine.

There was no evidence of analgesic potentiation by ceterizine when combined with acetaminophen or celecoxib or when loratadine was combined with naproxen sodium.

G. Swollen Throat Scale (SwoTS)

All four positive control drugs demonstrated greater reduction in throat swelling compared with placebo over 6 hours. Acetaminophen and celecoxib were shown to be significantly differentiated from placebo on this scale (both $p \leq 0.05$). This differentiation of known active analgesic drugs from placebo serves as a source of internal validation of the SwoTS. Ratings on the SwoTS correlated with ratings on the TSS ($r=0.74$, $p<0.0001$).

Figure 8:
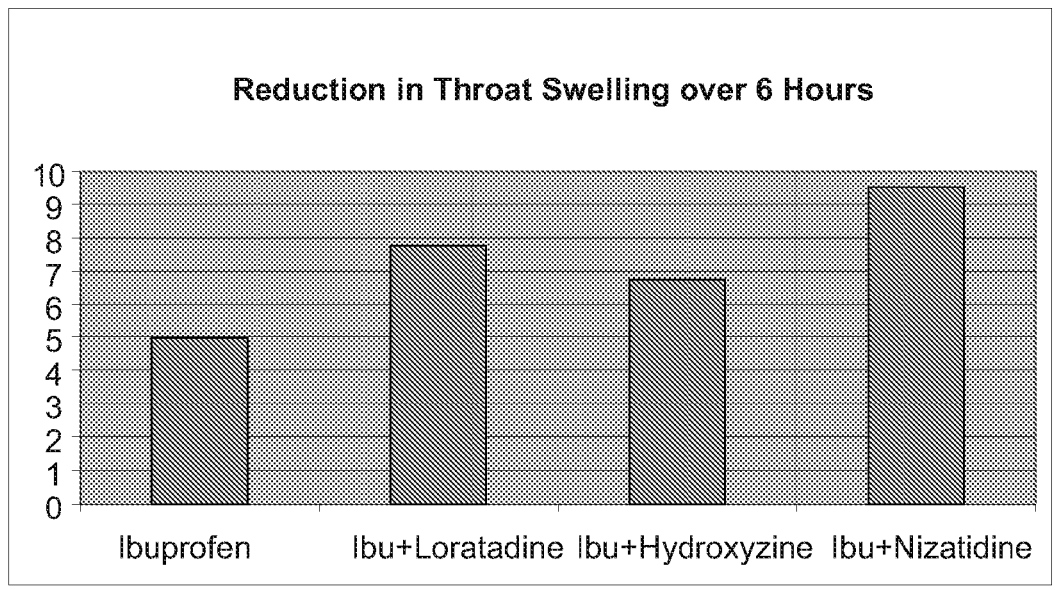
FIG. 8 shows the reduction in throat swelling over 6 hours of ibuprofen combinations and ibuprofen 200 mg.

With the exception of the comparison of naproxen/loratadine to placebo, all antihistamine/analgesic combinations differed from placebo. As seen in FIG. 8, the comparison of ibuprofen/loratadine to ibuprofen revealed 56% difference in the reduction of throat swelling over 6 hours, the comparison of ibuprofen/hydroxyzine to ibuprofen a 36% difference, and. the comparison of ibuprofen/nizatidine to ibuprofen a 90% difference in the reduction of throat swelling over 6 hours.

Figure 9:
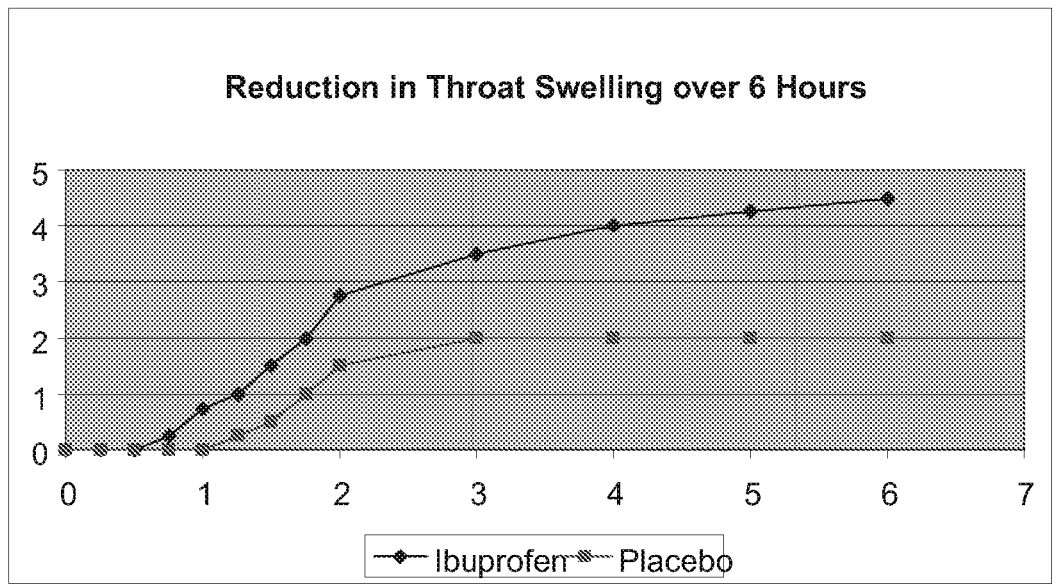
FIG. 9 shows the reduction in throat swelling at time points over 6 hours of ibuprofen 200 mg and placebo.

There was no evidence of enhanced overall analgesic effect on the SwoTS for the comparisons of acetaminophen/ceterizine, celecoxib/ceterizine, or naproxen/loratadine to each single analgesic. With the exception of naproxen/loratadine, all single- and combination-ingredient drugs also demonstrated greater reduction in throat swelling compared to placebo at individual time points with pharmacodynamic curves typical of analgesic drugs, as shown for ibuprofen compared with placebo in FIG. 9.

Because patients were admitted to the study regardless of the severity of their pre-treatment SwoTS (which ranged from 0 to 10, i.e., not $\geq 7$, as required for the TSS at baseline), these findings represent underestimates of treatment effects measured on the SwoTS. Given this range of low baseline values, it is noteworthy that analgesic activity was detected on the SwoTS even at early time points.

In sum, evidence of analgesic potentiation was detected on the SwoTS in three comparisons:
1. ibuprofen/hydroxyzine vs. ibuprofen, identifying analgesic potentiation by hydroxyzine;
2. ibuprofen/loratadine vs. ibuprofen, identifying analgesic potentiation by loratadine when combined with ibuprofen; and
3. ibuprofen/nizatidine vs. ibuprofen, identifying analgesic potentiation by nizatidine.

There was no evidence of analgesic potentiation by ceterizine when combined with acetaminophen or celecoxib or by loratadine when combined with naproxen sodium.

G. Quality of Pain Index (QPI)

There was greater reduction in the QPI (a summary index of 12 sensory, affective, and evaluative qualities of throat pain) by single analgesics compared with placebo over 6 hours. Acetaminophen and celecoxib were significantly differentiated from placebo on the QPI (both $p \leq 0.05$). This differentiation of known active analgesic drugs from placebo serves as a source of internal validation of the QPI. All antihistamine/analgesic combinations differed from placebo, too, further validating the QPI. Ratings on the QPI correlated with TSS ratings ($r=0.82$, $p<0.0001$).

Figure 10:
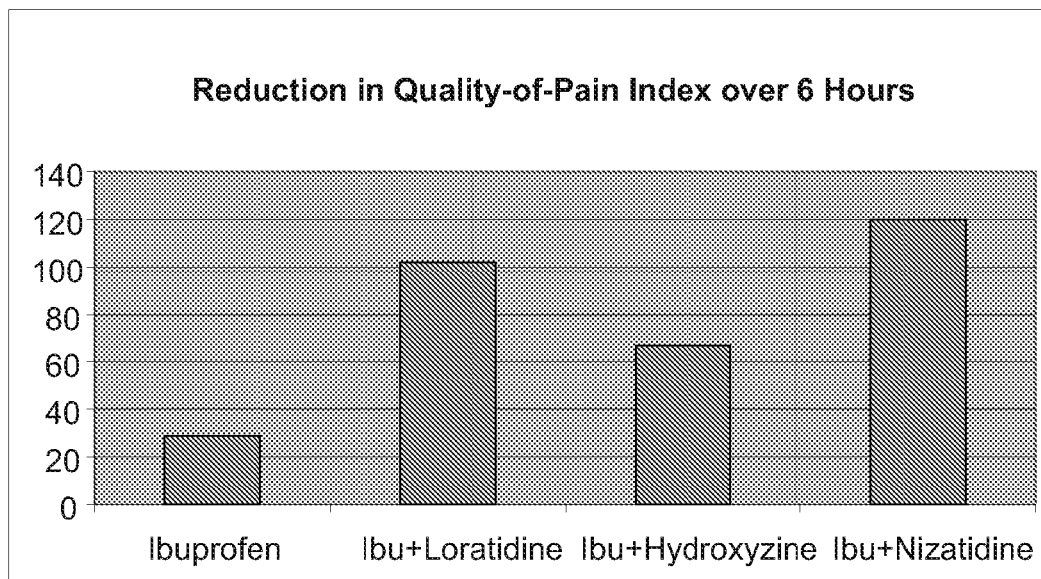
FIG. 10 shows the reduction in the Quality-of-Pain Index over 6 hours of ibuprofen combinations and ibuprofen 200 mg.

The comparison of ibuprofen/loratadine to ibuprofen revealed 250% difference in the reduction of qualities of throat pain over 6 hours (FIG. 10). The comparison of ibuprofen/hydroxyzine to ibuprofen revealed 130% difference in the reduction of qualities of throat pain over 6 hours. The comparison of ibuprofen/nizatidine to ibuprofen revealed 310% difference in the reduction of qualities of throat pain over 6 hours ($p=0.10$). There was no evidence of enhanced overall analgesic effect on the QPI for the comparisons of acetaminophen/ceterizine, celecoxib/ceterizine, or naproxen/loratadine to each single analgesic.

Because patients were admitted to the study regardless of the pre-treatment the severity of each of the 12 qualities of throat pain (which ranged from 0 to 10, i.e., not $\geq 7$, as required for the TSS at baseline), these findings represent underestimates of treatment effects measured on the QPI.

Figure 11:
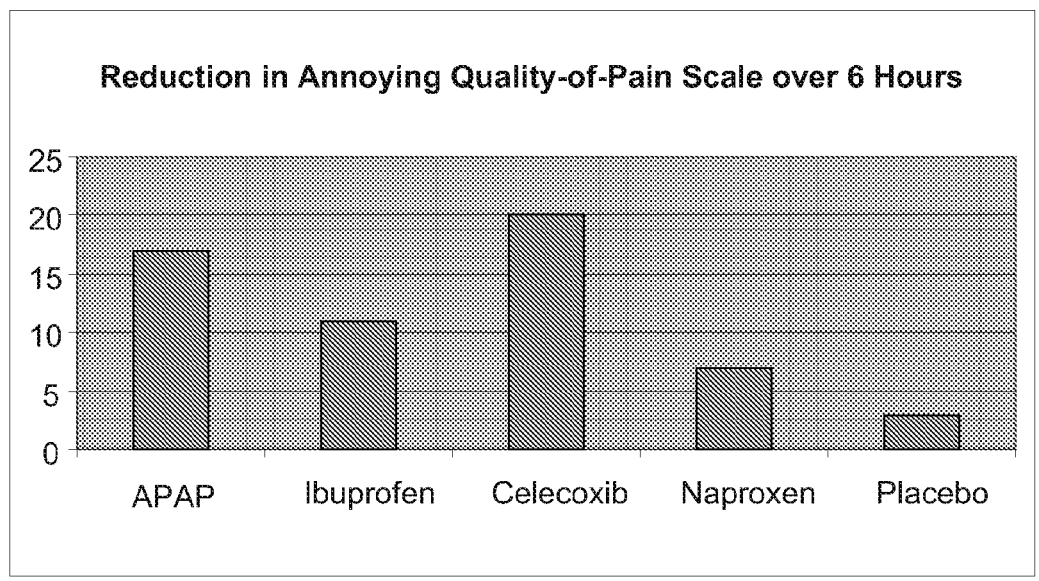
FIG. 11 shows the reduction in the Annoying Quality-of-Pain Scale over 6 hours of several analgesics and placebo.

Though we have not examined the responses on every quality-of-pain scale, we did notice responses on one scale that highlight the theme of this application (i.e., the sensitivity and utility of patient-oriented scales): patients' ratings on the annoying quality-of-pain scale (FIG. 11) identified clear differences between active drugs and placebo, thus validating the scale itself.

In sum, evidence of analgesic potentiation was detected on the QPI in three comparisons:
1. ibuprofen/loratadine vs. ibuprofen, identifying analgesic potentiation by loratadine when combined with ibuprofen;
2. ibuprofen/hydroxyzine vs. ibuprofen, identifying analgesic potentiation by hydroxyzine; and
3. ibuprofen/nizatidine vs. ibuprofen, identifying analgesic potentiation by nizatidine.

As on other scales, there was no evidence of analgesic potentiation by ceterizine when combined with acetaminophen or celecoxib or by loratadine when combined with naproxen sodium.

H. Most Bothersome Qualities of Pain (MBQs)

Analyses based on the qualities of pain that were most bothersome to the patient (i.e., the highest rated sensory, affective, or evaluative quality of throat pain for each patient at baseline) have not been performed.

J. Types of Throat Pain (Heat, Dryness, Soreness, Emotional, Function, Size)

Examination of the patients' ratings on each scale delineated six specific types of throat pain:

| Heat: | hot, burning | ["Hot throat"] |
| Dryness: | dry, raw, scratchy, tight, raspy | ["Dry throat"] |
| Soreness: | sore, hurts | ["Sore throat"] |
| Emotional: | annoying, irritating | ["Annoying throat"] |
| Function: | difficulty swallowing, difficulty talking | ["Can't swallow/talk"] |
| Size: | swollen | ["Swollen throat"] |

It was observed that patients reported some clusters of symptoms as more severe than others: for some patients "heat" was a predominant symptom complex, for others "soreness," etc. Analyses have not been performed comparing treatment responses among patients within each specific cluster (e.g., patients with a "dry throat" or a "swollen throat").

K. Safety and Tolerability

There were no serious adverse events or discontinuations due to an adverse event.

CONCLUSIONS

As measured on the primary rating scale (TSS), the positive control drugs acetaminophen, ibuprofen, celecoxib, and naproxen sodium were clearly distinguished from placebo. Each antihistamine/analgesic combination was also distinguished from placebo on the TSS. These findings provide internal validation of the study and its results: if known analgesics cannot be distinguished from placebo on a validated measurement instrument, the study model itself is deficient.

Using this standard scale, differences were detected between ibuprofen/loratadine and ibuprofen, between ibuprofen/hydroxyzine and ibuprofen, and between ibuprofen/nizatidine and ibuprofen.

The sensitivity of the new methods, moreover, was remarkable. Unlike the conventional requirement for a de minimis entry level (in this case, ≥7 on the TSS), there were no admission criteria for the new scales used herein, which ranged from 0 to 10 at baseline. Despite this "all-comer" study sample, the new scales used herein were used by the patients in each treatment group to measure impressive treatment effects between active drugs and placebo. Though tested in a small sample size (when statistically significant differences are less likely), some differences between single-ingredient analgesics and placebo were statistically significant, in fact. This clinical experiment repeatedly confirmed the ability of these new methods to measure pain status and detect changes after treatment and validated them as assays of analgesic activity.

The new scales used herein also identified differences between antihistamine/analgesic combinations and the respective single analgesics Several new measurement instruments (e.g., Difficulty Swallowing Scale, Difficulty Talking Scale, Throat Function Index, Swollen Throat Scale, Qualities of Pain Index) described herein indicated that hydroxyzine, loratadine, and nizatidine enhance the analgesic properties of ibuprofen. Wide differences (ranging from 20% to over 100%) were detected between ibuprofen/loratadine and ibuprofen, between ibuprofen/hydroxyzine and ibuprofen, and between ibuprofen/nizatidine and ibuprofen, evidence that was replicated consistently.

It is noteworthy, too, that the effects of the $H_1$-antagonist (hydroxyzine) and of the $H_2$-antagonist (nizatidine) appeared to provide not only greater analgesia but indications of a more prolonged duration of effect.

The most striking (and surprising) effect was noted in the comparison of ibuprofen with nizatidine to ibuprofen alone, a large difference that is attributable perhaps to the faster bioavailability of nizatidine powder in a capsule, compared to the slower bioavailability of ibuprofen in a coated and compressed tablet. (Thus, one possible administration schedule involves the pre-administration of an antihistamine to assure analgesic potentiation.) The wide differentiation of ibuprofen 200 mg/nizatidine 150 mg from ibuprofen 200 mg suggests, too, that this combination may confer the same or greater extent of analgesia as a 400-mg dose of ibuprofen (thus avoiding potential side effects associated with high dosages of NSAIDs), an example of "optimal analgesia" in the antihistamine/analgesic combination.

This study also had some negative findings. For example, there was no evidence that ceterizine potentiates analgesia when combined with acetaminophen or celecoxib. There was the suggestion, however, that ceterizine may hasten the onset of action of celecoxib: an adequately sized onset-of-action study might discern this feature of analgesic potentiation by ceterizine and other antihistamines.) Although loratadine does augment ibuprofen's analgesia (which was repeatedly detected on different measurement instruments), it appears that loratadine does not provide analgesic potentiation when combined with naproxen sodium, suggesting a pharmaceutical incompatibility or pharmacologic interaction (i.e., the naproxen sodium salt, unlike ibuprofen, may interfere with loratadine activity).

These findings are informative. Both the standard and the new methods were capable of distinguishing the single-ingredient analgesics from placebo as well as the antihistamine/analgesic combinations from placebo (i.e., they are sensitive measurement instruments). However, these methods did not identify analgesic potentiation for every combination. They discriminated additional analgesia only when it existed (i.e., only some antihistamine/analgesic combinations were shown to "work better" than the single analgesic). Altogether, these findings add credibility to the positive findings of the study.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for enhancing an analgesic response in a human desiring treatment for reducing acute pain which comprises orally administering to said human having acute pain a single dose composition comprising (i) an analgesic effective amount of a compound selected from the group consisting of naproxen and the pharmaceutically acceptable salt thereof at a dosage from 100 mg to 900 mg per single dose composition, and (ii) an analgesic potentiating amount of a compound selected from the group consisting of nizatidine and the pharmaceutically effective salt or isomer thereof at a dosage from 10 mg to 200 mg per single dose composition,
wherein said single dose composition comprises an admixture of (i) and (ii), wherein the single dose composition does not have an enteric coating so that (i) and (ii) are released concomitantly after administration to said human,
wherein said naproxen or the pharmaceutically acceptable salt thereof and said nizatidine or the pharmaceutically acceptable salt or isomer thereof provides an enhanced analgesic response in said human compared to the administration to said human of the same dosage strength of said naproxen or the pharmaceutically acceptable salt thereof in the absence of said nizatidine or the pharmaceutically acceptable salt or isomer thereof.

2. The method of claim 1, wherein said analgesic compound defined in (i) is 100 mg to 300 mg naproxen or the pharmaceutically acceptable salt thereof per single dose composition.

3. The method of claim 2, wherein said analgesic potentiating compound defined in (ii) is 50 mg to 100 mg nizatidine or the pharmaceutically acceptable salt or isomer thereof per single dose composition.

4. The method of claim 2, wherein said analgesic potentiating compound defined in (ii) is 10 mg to 50 mg nizatidine or the pharmaceutically acceptable salt or isomer thereof per single dose composition.

5. The method of claim 2, wherein said analgesic potentiating compound defined in (ii) is 50 mg of nizatidine or the pharmaceutically acceptable salt or isomer thereof per single dose composition.

6. The method of claim 2, wherein said analgesic potentiating compound defined in (ii) is 100 mg to 200 mg nizatidine or the pharmaceutically acceptable salt or isomer thereof per single dose composition.

7. The method of claim 2, wherein said analgesic potentiating compound defined in (ii) is 150 mg of nizatidine or the pharmaceutically acceptable salt or isomer thereof per single dose composition.

8. The method of claim 1, wherein said analgesic compound defined in (i) is 200 mg to 600 mg naproxen or the pharmaceutically acceptable salt thereof per single dose composition.

9. The method of claim 8, wherein said analgesic potentiating compound defined in (ii) is 50 mg to 100 mg nizatidine or the pharmaceutically acceptable salt or isomer thereof per single dose composition.

10. The method of claim 8, wherein said analgesic potentiating compound defined in (ii) is 10 mg to 50 mg nizatidine or the pharmaceutically acceptable salt or isomer thereof per single dose composition.

11. The method of claim 8, wherein said analgesic potentiating compound defined in (ii) is 50 mg of nizatidine or the pharmaceutically acceptable salt or isomer thereof per single dose composition.

12. The method of claim 8, wherein said analgesic potentiating compound defined in (ii) is 100 mg to 200 mg nizatidine or the pharmaceutically acceptable salt or isomer thereof per single dose composition.

13. The method of claim 8, wherein said analgesic potentiating compound defined in (ii) is 150 mg of nizatidine or the pharmaceutically acceptable salt or isomer thereof per single dose composition.

14. The method of claim 1, wherein said analgesic compound defined in (i) is naproxen sodium.

15. The method of claim 14, wherein said naproxen sodium is 220 mg per single dose composition.

16. The method of claim 15, wherein said analgesic potentiating compound defined in (ii) is 50 mg to 100 mg nizatidine or the pharmaceutically acceptable salt or isomer thereof per single dose composition.

17. The method of claim 15, wherein said analgesic potentiating compound defined in (ii) is 10 mg to 50 mg nizatidine or the pharmaceutically acceptable salt or isomer thereof per single dose composition.

18. The method of claim 15, wherein said analgesic potentiating compound defined in (ii) is 50 mg of nizatidine or the pharmaceutically acceptable salt or isomer thereof per single dose composition.

19. The method of claim 15, wherein said analgesic potentiating compound defined in (ii) is 100 mg to 200 mg nizatidine or the pharmaceutically acceptable salt or isomer thereof per single dose composition.

20. The method of claim 15, wherein said analgesic potentiating compound defined in (ii) is 150 mg of nizatidine or the pharmaceutically acceptable salt or isomer thereof per single dose composition.

21. The method of claim 14, wherein said naproxen sodium is 200 mg to 600 mg per single dose composition.

22. The method of claim 21, wherein said analgesic potentiating compound defined in (ii) is 50 mg to 100 mg nizatidine or the pharmaceutically acceptable salt or isomer thereof per single dose composition.

23. The method of claim 21, wherein said analgesic potentiating compound defined in (ii) is 10 mg to 50 mg nizatidine or the pharmaceutically acceptable salt or isomer thereof per single dose composition.

24. The method of claim 21, wherein said analgesic potentiating compound defined in (ii) is 50 mg of nizatidine or the pharmaceutically acceptable salt or isomer thereof single dose composition.

25. The method of claim 21, wherein said analgesic potentiating compound defined in (ii) is 100 mg to 200 mg nizatidine or the pharmaceutically acceptable salt or isomer thereof per single dose composition.

26. The method of claim 21, wherein said analgesic potentiating compound defined in (ii) is 150 mg of nizatidine or the pharmaceutically acceptable salt or isomer thereof per single dose composition.

27. The method of claim 1, wherein said analgesic compound defined in (i) is naproxen.

28. The method of claim 27, wherein said naproxen is 200 mg per single dose composition.

29. The method of claim 27, wherein said analgesic potentiating compound defined in (ii) is 50 mg to 100 mg nizatidine or the pharmaceutically acceptable salt or isomer thereof per single dose composition.

30. The method of claim 27, wherein said analgesic potentiating compound defined in (ii) is 10 mg to 50 mg nizatidine or the pharmaceutically acceptable salt or isomer thereof per single dose composition.

31. The method of claim 27, wherein said analgesic potentiating compound defined in (ii) is 50 mg of nizatidine or the pharmaceutically acceptable salt or isomer thereof single dose composition.

32. The method of claim 27, wherein said analgesic potentiating compound defined in (ii) is 100 mg to 200 mg nizatidine or the pharmaceutically acceptable salt or isomer thereof per single dose composition.

33. The method of claim 27, wherein said analgesic potentiating compound defined in (ii) is 150 mg of nizatidine or the pharmaceutically acceptable salt or isomer thereof per single dose composition.

34. The method of claim 1, wherein the analgesic compound defined in (i) and nizatidine or the pharmaceutically acceptable salt or isomer thereof are incorporated into a polymeric matrix.

35. The method of claim 1, wherein said naproxen or the pharmaceutically acceptable salt thereof and said nizatidine or the pharmaceutically acceptable salt or isomer thereof, provide a faster onset of pain reduction in said human compared to the administration to said human of the same dosage strength of said naproxen or the pharmaceutically acceptable salt thereof in the absence of said nizatidine or the pharmaceutically acceptable salt or isomer thereof.

36. The method of claim 1, wherein said administration of said naproxen or the pharmaceutically acceptable salt thereof and said nizatidine or the pharmaceutically acceptable salt or isomer thereof, provides pain relief of longer duration than the administration of said naproxen or the pharmaceutically acceptable salt thereof in the absence of said nizatidine or the pharmaceutically acceptable salt or isomer thereof.

37. The method of claim 1, wherein the human is an adult human.

38. The method of claim 1, wherein the acute pain is selected from the group consisting of sore throat, earache, toothache, muscular aches, backache, headache, sprained ankle, sinus pain, and joint pain.

* * * * *